US 6,539,245 B2

(12) United States Patent
Tsukada et al.

(10) Patent No.: US 6,539,245 B2
(45) Date of Patent: *Mar. 25, 2003

(54) BIOMAGNETIC FIELD MEASURING METHOD AND APPARATUS

(75) Inventors: Keiji Tsukada, Kashiwa; Akihiko Kandori, Hitachinaka; Kenichi Okajima, Mitaka; Hitoshi Sasabuchi, Mito; Hiroyuki Suzuki, Hitachinaka; Shoji Kondo, Hitachinaka; Yasuaki Komiyama, Hitachinaka, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/793,600

(22) Filed: Feb. 27, 2001

(65) Prior Publication Data

US 2001/0009975 A1 Jul. 26, 2001

Related U.S. Application Data

(63) Continuation of application No. 09/035,827, filed on Mar. 6, 1998.

(30) Foreign Application Priority Data

Mar. 7, 1997 (JP) .............................. 9-052769
Mar. 14, 1997 (JP) .............................. 9-060488

(51) Int. Cl.$^7$ .............................................. A61B 5/05
(52) U.S. Cl. ................ 600/409; 600/425; 600/481; 600/509; 600/512; 600/516; 600/517; 324/244; 324/248
(58) Field of Search ................ 600/409, 425, 600/481, 509, 512, 516, 517, 523, 524; 324/244, 248

(56) References Cited

U.S. PATENT DOCUMENTS 5,170,119 A 12/1992 Sekihara et al.
5,204,624 A 4/1993 Ueda (List continued on next page.)

FOREIGN PATENT DOCUMENTS

| JP | 2-249530 | 10/1990 |
| JP | 6-121776 | 5/1994 |
| JP | 8-266499 | 10/1996 |
| JP | 10-305019 | 11/1998 |

OTHER PUBLICATIONS

Japanese Journal of Medical Instrumentation, vol. 66, No. 10, 1996, pp. 623–624.
Journal of Electrocardiology, vol. 9, No. 4, 1976, pp. 426–432.

(List continued on next page.)

Primary Examiner—Marvin M. Lateef
Assistant Examiner—Jeoyuh Lin
(74) Attorney, Agent, or Firm—Mattingly, Stanger & Malur, P.C.

(57) ABSTRACT

A biomagnetic field measuring apparatus has a plurality of fluxmeters disposed externally of a living body and each including a superconducting quantum interference device (SQUID) for detecting a biomagnetic field generated from the living body, the plurality of fluxmeters being operative to detect a temporal change of a component of the biomagnetic field in a first direction which is vertical to the surface of the living body, an operation processor for performing computation for determining a temporal change of a value proportional to a root of square sum of differential value of the first-direction magnetic field component in second and third directions which cross the first direction and computation for integrating the temporal change of the value over a predetermined interval to determine an integral value, and a display for displaying the determined integral value. Distribution of magnetic fields generated from the heart is determined with a small number of fluxmeters.

7 Claims, 22 Drawing Sheets

U.S. PATENT DOCUMENTS

| | | |
|---|---|---|
| 5,206,589 A | 4/1993 | Kado et al. |
| 5,211,178 A | 5/1993 | Kado et al. |
| 5,228,443 A | 7/1993 | Tatar |
| 5,285,385 A | 2/1994 | Igarashi et al. |
| 5,426,365 A | 6/1995 | Sekihara et al. |
| 5,526,811 A | 6/1996 | Lypchuk |
| 5,752,514 A | 5/1998 | Okamura et al. |
| 6,230,037 B1 * | 5/2001 | Tsukada et al. ............ 600/409 |

OTHER PUBLICATIONS

Review of the Scientific Instruments, vol. 66, No. 10, 1995, pp. 5085–5091.

Tenth International Conference on Biomagnetism, Feb. 17, 1996, Y. Yoshida et al, p. 351.

Tenth International Conference on Biomagnetism, Feb. 17, 1996, K. Tsukada et al, p. 248.

Circulation 63, No. 5, 1981, pp. 1166–1172.

Phys. Med. Biol., vol. 32, No. 1, 1987, pp. 11–22.

* cited by examiner

BIOMAGNETIC FIELD MEASURING METHOD AND APPARATUS

This is a continuation application of U.S. Ser. No. 09/035,827, filed Mar. 6, 1998.

BACKGROUND OF THE INVENTION

The present invention relates to a biomagnetic field measuring method and apparatus for measuring a biomagnetic field generated by a nerve action of the brain as well as a myocardial action of the heart of a living body by using a plurality of fluxmeters each consisting of a highly sensitive superconducting quantum interference device (SQUID).

In addition to a magnetic field generated by a current dipole, a magnetic field due to a volume current flowing in the living body is enumerated as a biomagnetic field. Measurement of a normal component ($B_z$: z component in the Cartesian coordinate system or $B_r$: radius component in the polar coordinate system) is considered to be hardly affected by the volume current. In conventional techniques, the plane of a detection coil connected to a SQUID is disposed in parallel to the body surface to measure $B_z$ or $B_r$ which is a normal component to the body surface. Results of the biomagnetic field measurement are displayed in the form of a temporal change waveform of the measured field component or an isomagnetic field map (contour map) for connecting points at which magnitudes of the magnetic field component measured at desired time points are equal to each other. Various analysis methods have been proposed which analyze a magnetic field source participating in generation of the biomagnetic field from the obtained isomagnetic field map and a typical one, analysis is carried out by replacing the magnetic field source with a current dipole.

An isomagnetic field map of a normal component ($B_z$ or $B_r$) of the magnetic field generated by a current dipole is of a pattern having a source pole of the magnetic field and a sink pole of the magnetic field at positions which are separate from each other from the center where a magnetic field source (current dipole) is positioned. The magnitude, position and direction of the magnetic field source (current dipole) are analyzed in accordance with magnitudes of the magnetic field at the two poles and a distance therebetween.

In a first prior art (H. Hosaka and D. Cohen: J. Electrocardiology, 9 (4), pp. 426–432 (1976)), a method is employed for displaying current sources distributed in the myocardium by using an isomagnetic field map of a measured normal component $B_z$ with the aim of promoting visualizing of direction and intensity of currents in the myocardium and according to this method, an arrow map is contrived for expressing a current vector J (x, y) defined by equation (1) on measuring points by using an arrow. In the following description, Gothic characters are used to indicate vectors.

$$J(x, y) = (\partial B_z(x, y)/\partial y)e_x - (\partial B_z(x, y)/\partial x)e_y \quad (1)$$

In equation (1), $e_x$ designates a unit vector in x direction and $e_y$ designates a unit vector in y direction. This prior art, however, encounters a problem that when a plurality of current sources exist, it is difficult to discriminate the individual current sources from each other on the basis of the isomagnetic field map of normal component $B_z$.

In a second prior art (K. Tukada et al: Review of the Scientific Instruments, 66(10), pp. 5085–5091 (1995)), for the sake of visualizing a plurality of distributed current sources, the normal component ($B_z$ or $B_r$) is not detected but tangential components $B_x$ and $B_y$ are measured by using a detection coil whose plane is disposed vertically to the body surface. Each of the measured tangential components $B_x$ and $B_y$ is displayed in the form of an isomagnetic field map. The tangential components $B_x$ and $B_y$ measured according to the second prior art are considered to be affected by the volume current, but, in an isomagnetic field map of two-dimensional vector magnitude $B_{xy}$ obtained by synthesizing $B_x$ and $B_y$ measured at time point t pursuant equation (2), a peak can always be obtained directly above a current dipole and therefore, even when a plurality of current dipoles exist, individual current dipoles can be separated for visualization.

$$|B_{xy}(x, y, t)| = \sqrt{\{(B_x(x, y, t))^2 + (B_y(x, y, t))^2\}} \quad (2)$$

In a third prior art (Y. Yoshida et al: Tenth International Conference on Biomagnetism, Santana Fe, New Mexico, Feb. 17 (1996)), a normal component and two tangential components of a biomagnetic field are detected by using a vector magnetic field sensor consisting of three detection coils having coil planes which are orthogonal to each other, detection results of the magnetic field components are converted in terms of the Cartesian coordinate system to determine Cartesian coordinate system components $B_x$, $B_y$ and $B_z$, and an isomagnetic field map of the normal component $B_z$ and an isomagnetic field map of two-dimensional vector magnitude $B_{xy}$ are displayed, respectively.

In a fourth prior art (K. Tsukada et al: Tenth International Conference on Biomagnetism, Santa Fe, N. Mex., Feb. 17 (1996)), two tangential components $B_x$ and $B_y$ of a biomagnetic field are detected and an isomagnetic field map based on $|B_{xy}| = |B_x + B_y|$ is compared with an isomagnetic field map based on a normal component $B_z$.

As diagrams for indicating measurement results of electrical physiological phenomena in a living body, there are a magnetoencephalogram (MEG) obtained through measurement using a magnetoencephalogram and an electrocardiogram (ECG) obtained through measurement using an electrocardiograph. In measurements of the electrocardiogram, a body surface potential map for mapping an electrocardiographic figure by using a plurality of electrodes is of a well-known technique. The MEG or the body surface potential map is depicted in the form of an isopotential map for connecting isopotential points.

In a fifth prior art (T. J. Montague et al: Circulation 63, No. 5, pp.1166–1172 (1981)), an isointegral map obtained by integrating a temporal change waveform of an output of each one of a plurality of electrodes over a desired time interval is depicted as a body surface potential map.

In the following description, "biomagnetic field" means "magnetic field generated from a living body", "cardiac magnetic field measurement" means "measurement of a magnetic field generated from the heart", and "cardiac magnetic waveform" means "waveform indicated by a magnetocardiogram (MCG) obtained through cardiac magnetic field measurement". Further, "encephalic magnetic field measurement" means "measurement of a magnetic field generated from the brain" and "encephalic magnetic waveform" means "waveform indicated by a magnetoencephalogram (MEG) obtained through encephalic magnetic field measurement".

Each of the conventional isomagnetic field maps of the respective components has inherent features. In the presence of a single current dipole, the position, magnitude and direction of a current source can be analyzed with ease by using the isomagnetic field map of normal component $B_z$. On the other hand, the isomagnetic field map of two-dimensional vector magnitude $B_{xy}$ obtained from measurement results of tangential components $B_x$ and $B_y$ features that even in the presence of a plurality of current dipoles, individual current dipoles can easily be discriminated from each other. But, for detection of a magnetic field, coils are required to be provided in x and y directions and the number of coils is doubled as compared to detection of only the normal component $B_z$. In vector measurement for measuring all the components $B_x$, $B_y$ and $B_z$, the number of required coils is tripled as compared to detection of only the normal component $B_z$. Accordingly, the magnetic field sensor consisting of a detection coil and a SQUID is increased in number, and in addition, the signal processing circuit and the like are also increased in number, raising a problem that the biomagnetic field measuring system becomes an expensive one. Further, the first prior art is disadvantageous in that arrows are merely indicated on measuring points and detailed distribution states of current sources are hardly discriminated.

From the isomagnetic field map indicated in terms of a biomagnetic field component, the position, magnitude and direction, at a desired time point, of a current source in a living body can be analyzed and detailed information about changes in position, magnitude and direction of the current source can be known. Conventionally, dynamic changes in various kinds of information pieces are captured by using many figures displayed on or delivered to the apparatus so as to diagnose a disease. In the prior art, however, many diagrams or maps indicating various kinds of information pieces are needed for diagnosis, and abnormality of changes in various kinds of information pieces is known empirically. As will be seen from the above, in the prior art, the processing of displaying, on a single map, systematic information as to what magnitude of current flows through which portion of a living body and as to which region an abnormal bio-current passes through is not executed. In the case of the body surface potential map, an isointegral technique was reported. This isointegral map was drawn by connecting between the same integral values over a desired time interval (for example, a time interval during which waves of Q, R and S are generated, and a time interval during which S to T waves are generated). The advantage of this isointegral map is that information of the heart can be obtained from only a single electrocardiographic figure. But in the isopotential map when the current source in the heart is assumed to be a single current dipole, a figure results disadvantageously in which an positive peak and a negative peak do not exist immediately above the current dipole but exist at a position which is separate from a point immediately above the current dipole. Further, when the position of the current dipole remains unchanged but the direction of the current dipole changes, the anode and cathode peak positions change, raising a problem that when potential is integrated, correspondence between the current source and the peak of an integral value is impaired. Like the case of the electrocardiogram, mere integration of a component of a biomagnetic field obtained through biomagnetic field measurement faces a problem that the peak position of the biomagnetic field component does not correspond to the position of the current source. Further, with only the isointegral map obtained from the electrocardiogram, because of individual differences such as the position and size of internal organs, it is difficult to accurately determine an abnormality such as a disease by simply gathering from the isointegral map.

SUMMARY OF THE INVENTION

An object of the present invention is to provide a biomagnetic field measuring method and apparatus which can grasp the whole state of a living body portion by using maps which are greatly reduced in number as compared to the maps required in the prior art.

Another object of the present invention is to provide a biomagnetic field measuring method and apparatus which can permit analysis of a magnetic field source by measuring a vertical component $B_z$ of a biomagnetic field without increasing the number of detection coils.

According to the present invention, (1) a biomagnetic field measuring method comprises: a first step of measuring a temporal change of a component of a biomagnetic field generated from a living body by using a plurality of fluxmeters disposed externally of the living body and each including a superconducting quantum interference device (SQUID), the magnetic field component being in a first direction which is vertical to the surface of the living body; a second step of determining a temporal change of a value proportional to a root of square sum of differential values of the first-direction magnetic field component in second and third directions which cross the first direction; a third step of integrating the temporal change of the value obtained in the second step over a predetermined interval to determine an integral value, and a fourth step of displaying the integral value obtained in the third step.

According to the present invention, (2) a biomagnetic field measuring method comprises: a first step of measuring temporal changes of components of a biomagnetic field generated from a living body by using a plurality of fluxmeters disposed externally of the living body and each including a superconducting quantum interference device (SQUID), the magnetic field components being in first and second directions which are parallel to the surface of the living body; a second step of determining a temporal change of a value proportional to a root of square sum of the first-direction and second-direction magnetic field components; a third step of integrating the temporal change of the value obtained in the second step over a predetermined time interval to determine an integral value; and a fourth step of displaying the integral value obtained in the third step.

Specifically, in the biomagnetic field measuring methods (1) and (2) as above, the above integral values are used through interpolation and extrapolation to display an isointegral map for connecting points at which the integral values in the above fourth step are equal to each other, the above third step of integrating the temporal change of the value obtained in the second step over a predetermined time interval to determine the integral value is carried out over a plurality of predetermined time intervals to determine a plurality of integral values, and computation for determining any of the ratio, the sum or the difference between the plurality of integral values is carried out. In the Cartesian coordinate system (x, y, z), the direction normal to the body surface is defined as z axis, the first direction is defined as z direction, the second direction is defined as x direction and the third direction is defined as y direction. In the polar coordinate system (r, θ, φ), the direction normal to the body surface is defined as r axis, the first direction is defined as r direction, the second direction is defined as θ direction and the third direction is defined as φ direction.

According to the present invention, (1) a biomagnetic field measuring apparatus for measuring biomagnetic field distribution comprises: a plurality of fluxmeters disposed externally of a living body and each including a superconducting quantum interference device (SQUID) for detecting, as a signal, a biomagnetic field generated from the living body; an operation processing unit for performing the operation processing of the signal; a and display unit for displaying a result of the operation processing. In the biomagnetic field measuring apparatus, the fluxmeters detect a temporal change of a component of a biomagnetic field, the magnetic field component being in a first direction which is normal to the surface of the living body, the operation processing unit performs computation for determining a temporal change of a value proportional to a root of square sum of differential values of the first-direction magnetic component in second and third directions which cross the first direction and computation for integrating the temporal change of the value over a predetermined time interval to determine an integral value, and the display unit displays the integral value.

According to the present invention, (2) in the above biomagnetic field measuring apparatus, the fluxmeters detect temporal changes of components of a biomagnetic field, the magnetic field components being in first and second directions which are parallel to the surface of the living body, the operation processing unit performs computation for determining a temporal change of a value proportional to a root of square sum of the first-direction and second-direction magnetic components and computation for integrating the temporal change of the value over a predetermined interval to determine an integral value, and the display unit displays the integral value.

Specifically, in the biomagnetic field measuring apparatus in (1) and (2) as above, an isointegral map for connecting points at which the integral values are equal to each other is obtained through interpolation and extrapolation and displayed on the display unit, and the operation processing unit carries out the computation of integrating the temporal change of the value over a predetermined time interval to determine the integral value over a plurality of predetermined time intervals to determine a plurality of integral values and computation for determining any of the ratio, the sum or the difference between the plurality of integral values, and the plurality of fluxmeters are disposed at equal intervals on the surface of the living body.

In the biomagnetic field measuring apparatus of the present invention, components of a magnetic field generated from the heart, that is, a normal component and a tangential component which are respectively normal and parallel to the chest surface can be displayed simultaneously. In the Cartesian coordinate system (x, y, z), when the direction normal to the living body surface is assumed to be z axis, the first direction is defined as z direction, the second direction is defined as x direction and the third direction is defined as y direction. In the polar coordinate system (r, θ, φ), when the direction normal to the living body surface is assumed to be r axis, the first direction is defined as r direction, the second direction is defined as θ direction and the third direction is defined as φ direction.

Essentially, in the present invention, when the direction normal to the living body surface is assumed to be z axis of the Cartesian coordinate system (x, y, z) and the plane parallel to the living body surface is assumed to be (x, y) plane, a normal component $B_z(x, y)$ of biomagnetic field normal to the body surface is detected, and tangential components $B_x$ and $B_y$ of biomagnetic field parallel to the body surface are estimated from differential values of the normal component $B_z$ in the x and y directions, respectively.

According to the present invention, without resort to detection coils for measuring the tangential components $B_x$ and $B_y$, an isomagnetic field map indicative of projection of current distribution upon the two-dimensional (x, y) plane can be obtained, a current source in the living body can be decided from a peak pattern in the isomagnetic field map, and (x, y) coordinate positions of a plurality of current dipoles can be known.

The contents of the operation processing carried out by the operation processing unit (a computer such as a personal computer for collecting signals detected by a plurality of fluxmeters and applying the following operation processing to the collected signals or an electronic circuit in the form of hardware dedicated to the operation processing) will be described.

When a plurality of fluxmeters each including a superconducting quantum interference device (SQUID) are used to detect tangential components (parallel to the surface of a living body) $B_x(x, y, t)$ and $B_y(x, y, t)$ of a magnetic field generated from the living body at a position (x, y) on the body surface (where in the Cartesian coordinate system (x, y, z), the plane parallel to the body surface is assumed to be xy plane and the axis perpendicular to the body surface is assumed to be z), two-dimensional vector magnitude $|B_{xy}(x, y)|$ (hereinafter, | | represents absolute value) is determined from a root of square sum of the tangential components $B_x(x, y, t)$ and $B_y(x, y, t)$ pursuant to equation (3).

$$|B_{xy}(x, y, t)| = \sqrt{\{(B_x(x, y, t))^2 + (B_y(x, y, t))^2\}} \quad (3)$$

Subsequently, an integral value $I_1(x, y)$ of waveform $|B_{xy}(x, y, t)|$ at each point (x, y) is obtained over a desired interval pursuant to equation (4), an isointegral map for connecting points at which the integral values $I_1(x, y)$ at respective points (x, y) are equal to each other is obtained through interpolation and extrapolation, and the isointegral map is displayed on the display screen.

$$I_1(x, y) = \int |B_{xy}(x, y, t)| dt \quad (4)$$

Hereinafter, presumption of the tangential components $B_x$ and $B_y$ from the measured magnetic field component $B_z(x, y, t)$ normal to the body surface will be described.

By taking advantage of the fact that the tangential component of biomagnetic field parallel to the body surface best reflects a current flowing through a portion immediately below the body surface and considering the relation between the current flow direction and the magnetic field direction, current distribution in the living body projected upon a two-dimensional plane parallel to the body surface can be surveyed by rotating a tangential vector ($B_x$, $B_y$) of the measured magnetic field counterclockwise through 90°. More particularly, where $e_x$ and $e_y$ represent unit vectors in x-axis and y-axis directions, a current vector J indicated by equation (5) can be determined from the tangential components $B_x$ and $B_y$ at respective measuring points and can be expressed in terms of distribution (arrow map) of current vector fields at the respective measuring points (x, y).

$$J = -B_y e_x + B_x e_y \quad (5)$$

On the other hand, considering the normal component $B_z$ of magnetic field perpendicular to the body surface, an arrow map using a current vector expressed by equation (1) is defined (the first prior art: H. Hosaka and D. Cohen (1976)).

$$J = (\partial B_z/\partial y)e_x - (\partial B_z/\partial x)e_y \quad (1)$$

Comparing equation (1) with equation (5), the present inventors have found the possibility that equations (6) and (7) are satisfied, that is, the possibility that the tangential components $B_x$ and $B_y$ can be induced from the normal component $B_z$ of the measured magnetic field and have studied in various ways. Results of studies will be described hereunder in greater detail.

$$B_x - (\partial B_z/\partial x) \tag{6}$$

$$B_y - (\partial B_z/\partial y) \tag{7}$$

FIG. 1 is a diagram useful for explaining the modeling of the generation of a magnetic field due to action of the heart (cardiac magnetic field) by a magnetic field generated from a current dipole in a horizontally layered conductor and analyzing the model. In FIG. 1, P designates a horizontally layered conductor having its surface on the xy plane of the Cartesian coordinate system (x, y, z), Q designates the moment of a current dipole existing at a position indicated by a position vector $r_0$ ($x_0$, $y_0$, $z_0$), and r(x, y, z) designates a position vector of a measuring point at which magnetic flux density B(r) (magnetic field) is measured. In the model shown in FIG. 1, a magnetic field B(r) generated outside the horizontally layered conductor P is formulated by Sarvas (literature: Phys. Med. Biol., Vol. 32, No. 1, pp.11–22 (1987)) and is expressed by equation (8).

$$B(r) = \{\mu_0/(4\pi K^2)\}\{Q \times a \cdot e_z \nabla K - K e_z \times Q\} \tag{8}$$

In equation (8), $\mu_0$ designates magnetic permeability of vacuum, $e_z$ designates a unit vector in z-axis direction, "x" designates vector product, "·" designates scalar product, and $\nabla$ designates grad ($\partial/\partial x$, $\partial/\partial y$, $\partial/\partial z$). Then, a is indicated by equation (9), a is indicated by equation (10), K is indicated by equation (11) and $\nabla K$ is indicated by equation (12). | | indicates absolute value.

$$a = r(x, y, z) - r_0(x_0, y_0, z_0) \tag{9}$$

$$a = |a| \tag{10}$$

$$K = a(a + a \cdot e_z) \tag{11}$$

$$\nabla K = (2 + a^{-1} a \cdot e_z) a + a e_z \tag{12}$$

Tangential components $B_x$ and $B_y$ of the B (r) given by equation (8) which are parallel to the horizontally layered conductor P and normal component $B_z$ normal to the horizontally layered conductor P are given by equations (13), (14) and (15), respectively.

$$B_x = \{\mu_0/(4\pi K^2)\} \times [\{Q_x(y-y_0) - Q_y(x-x_0)\}(\nabla K)_x + K Q_y] \tag{13}$$

$$B_y = \{\mu_0/(4\pi K^2)\} \times [\{Q_y(y-y_0) - Q_x(x-x_0)\}(\nabla K)_x + K Q_x] \tag{14}$$

$$B_z = \{\mu_0/(4\pi K^2)\} \times [\{Q_x(y-y_0) - Q_y(x-x_0)\}(\nabla K)_z] \tag{15}$$

On the other hand, a differential value in x direction of the normal component Bz indicated by equation (13) is expressed by equation (16).

$$\partial B_z/\partial x = \{\mu_0/(4\pi K^2)\} \times [\{Q_x(y-y_0) - Q_y(x-x_0)\}\{-2(\nabla K)_z(\nabla K)_x/K - a^{-3}(x-x_0)(z-z_0)^2 + a^{-1}(x-x_0)\} - (\nabla K)_z Q_y] \tag{16}$$

Similarly, a differential value in y direction of the normal component $B_z$ is expressed by equation (17).

$$\partial B_z/\partial y = \{\mu_0/(4\pi K^2)\} \times [\{Q_x(y-y_0) - Q_y(x-x_0)\}\{^2(\nabla K)_z(\nabla K)_y/K + a^{-3}(y-y_0)(z-z_0)^2 - a^{-1}(y-y_0)\} + (\nabla K)_z Q_x] \tag{17}$$

In equations (16) and (17), $$\alpha = (\nabla K)_z/K \tag{18}$$

$$\beta_x = -a^{-3}(x-x_0)(z-z_0)^2 + a^{-1}(x-x_0) \tag{19}$$

$$\beta_y = -a^{-3}(y-y_0)(z-z_0)^2 + a^{-1}(y-y_0) \tag{20}$$

and equations (16) and (17) are reduced to equations (21) and (22).

$$\partial B_z/\partial x = -\{\mu_0/(4\pi K^2)\} \times [\{Q_x(y-y_0) - Q_y(x-x_0)\}\{2\alpha(\nabla K)_x \beta_x\} + \alpha K Q_y]) \tag{21}$$

$$\partial B_z/\partial y = -\{\mu_0/(4\pi K^2)\} \times [[\{Q_x(y-y_0) - Q_y(x-x_0)\}\{2\alpha(\nabla K)_y - \beta_y\} + \alpha K Q_x] \tag{22}$$

For simplification, equations (13), (21), (14) and (22) are normalized by a common Lactor $\{\mu_0/(4\pi K^2)\}$ so as to be reduced to equations (13'), (21'), (14') and (22').

$$B_x = (\nabla K)_x \{Q_x(y-y_0) - Q_y(x-x_0)\} + K Q_y \tag{13'}$$

$$\partial B_z/\partial x = -2\alpha(\nabla K)_x \{Q_x(y-y_0) - Q_y(x-x_0)\} - \alpha K Q_y$$

$$+ \beta_x \{Q_x(y-y_0) - Q_y(x-x_0)\} = -2\alpha B_x + \alpha K Q_y + \beta_x \{Q_x(y-y_0) - Q_y(x-x_0)\} \tag{21'}$$

$$B_y = (\nabla K)_y \{Q_x(y-y_0) - Q_y(x-x_0)\} + K Q_x \tag{14'}$$

$$\partial B_z/\partial y = -2\alpha(\nabla K)_y \{Q_x(y-y_0) - Q_y(x-x_0)\} - \alpha K Q_x]$$

$$+ \beta_y \{Q_x(y-y_0) - Q_y(x-x_0)\} = -2\alpha B_y + \alpha K Q_x + \beta_y \{Q_x(y-y_0) - Q_y(x-x_0)\} \tag{22'}$$

As will be seen from equations (13') and (21'), the value of $\partial B_z/\partial x$ equals a value obtained by adding two additional terms to a term equal to $-2\alpha$ times the tangential component $B_x$ and as will be seen from equations (14') and (22'), the value of $\partial B_z/\partial y$ equals a value obtained by adding two additional terms to a term equal to $-2\alpha$ times the tangential component $B_y$.

When moment $Q = (Q_x, Q_y, 0)$, where $Q_x = Q_y = 50$ [nAm], exists at a point $r_0(0, 0, -z_0)$, where $z_0 = 0.05$ [m], inside the horizontally layered conductor P as shown in schematic positional relation of FIG. 2, $B_x$ (equation (13)) is compared with $-\partial B_z/\partial x$ (equation (16)). By substituting $x_0 = y_0 = y = 0$ and $Q_0 = 0$ into equations (13) and (16), equations (23) and (24) are obtained.

$$B_x(x,0) = \{\mu_0/(4\pi K^2)\}\{-(\nabla K)_x Q_y x + K Q_y\} \tag{23}$$

$$\partial B_z(x,0)/\partial x = \{\mu_0/(4\pi K^2)\}\{2\alpha(\nabla K)_x Q_y x - \alpha K Q_y - \beta_x Q_y X\} \tag{24}$$

FIG. 3 shows $B_x$ (equation (23)) and $-\partial B_z/\partial x$ (equation (24)) on the horizontally layered conductor P in terms of relative magnetic field magnitude curves $C_1$ and $C_2$ which are normalized by maximum values of $B_x$ and $-\partial B_z/\partial x$. More specifically, the curve $C_1$ represents $B_x(x, 0)/\max|b_x(x, 0)|$ and the curve $C_2$ represents $\{-\partial B_z(x, 0)/\partial x\}/\max|\partial B_z(x, 0)/\partial x|$. As will be seen from FIG. 3, the distribution of each of the $B_x$ and $-\partial B_z/\partial x$ has a peak at the original (x=0) which is immediately above the existence of the current dipole, indicating that the maximum signals of both the $B_x$ and $-\partial B_z/\partial x$ can be detected when the measuring point is immediately above the point where the current dipole exists. The curve $C_2$ has a sharper peak than the curve $C_1$, indicating that the magnetic field distribution due to $-\partial B_z/\partial x$ (equation (16)) has higher spatial resolution than the magnetic field distribution due to $B_x$ (equation (13)).

Magnetic field magnitude curves $C_3$, $C_4$ and $C_5$ depicted in FIG. 4 represent the first, second and third terms of $-\partial B_z(x, 0)/\partial x$, respectively. Gathering from the results shown in FIG. 4, the third term is negligible in relation to the first and second terms, so that the shape of $-\partial B_z(x, 0)/\partial x$ can be deemed to be determined by the first and second terms and equation (24) can be approximated by equation (24–).

$$\partial B_z(x,0)/\partial x = \{\mu_0/(4\pi K^2)\}(2\alpha(\nabla K)_x Q_y x - \alpha K Q_y) \tag{241}$$

FIG. 5 shows curves indicative of magnitude of relative magnetic field obtained by comparing the first term with the second term of each of the equations (13) and (16) after normalization. In FIG. 5, curve $C_6$ represents {first term of $B_x(x, 0)$}/$\max|B_x(x, 0)|$, that is, $\{-(\nabla K)_x Q_y x\}/\max|B_x(x, 0)|$, curve $C_7$ represents {first term of $-\partial B_z(x, 0)/\partial x$}/max|$\partial B_z(x, 0)/\partial x$|, that is, $\{-2\alpha(\nabla K)_x Q_y x\}$/max|$\partial B_z(x, 0)/\partial x$|, curve $C_8$ represents {second term of $B_x(x, 0)$}/max|$B_x(x, 0)$|, that is, $\{KQ_y\}$/max|$B_x(x, 0)$|, and curve $C_9$ represents {second term of $\partial b_z(x, 0)/\partial x$}/max|$\partial B_z(x, 0)/\partial x$|, that is, $\{\alpha KQ_y\}$/max|$\partial B_z(x, 0)/\partial x$|.

The results of FIG. 5 show that the distribution of each of the first and second terms of $-\partial B_z(x, 0)/\partial x$ is sharper than the distribution of each of the first and second terms of $B_x(x, 0)$ and the sharpness of the distribution is prescribed by $\alpha=(\nabla K)_z/K$ defined by equation (18).

In FIG. 6, magnetic field curve $C_{10}$ represents $\alpha=(\nabla K)_z/K$, magnetic field curve $C_{11}$ represents $-\{$first term of equation (24)$\}/\{$first term of equation (23)$\}$, that is, $2\alpha(\nabla K)_x Q_y x/(\nabla K)_x Q_y x = 2\alpha$, and magnetic field curve $C_{12}$ represents $-\{$second term of equation (24)$\}/\{$second term of equation (23)$\}$, that is, $\alpha KQ_y/KQ_y=\alpha$. As shown in FIG. 6, $\alpha=(\nabla K)_z/K$ (curve $C_{10}$) has a peak point at the original where the current dipole exists, and the peak value is $2/(z-z_0)$. The magnitude of $-\partial B_z(x, 0)/\partial x$ differs from that of $B_x(x, 0)$ by $2/(z-z_0)$ at the peak point. The current dipole exists at a depth indicated by $(z-z_0)$. It is difficult to determine $(z-z_0)$ from practical measurement of magnetic field. By comparing equations (23) and (24'), equation (25) is obtained.

$$\partial B_x(x,0)/\partial x = \{\mu_0/(4\pi K^2)\}\{-2\alpha(\nabla K)_x Q_y x + \alpha KQ_y\} = 2\alpha B_x(x,0) - \{\mu_0/(4\pi K)\}\alpha Q_y \quad (25)$$

Namely, when the second term is smaller than the first term in equation (25), approximate equation (26) is deemed to be satisfied.

$$-\partial B_z(x,0)/\partial x = 2\alpha B_x(x,0) \quad (26)$$

In generalization, when two additional terms other than $-2\alpha B_x$ are smaller than $-2\alpha B_x$ in equation (21'), approximate equation (27) is deemed to be satisfied.

$$\partial B_z/\partial x = -2\alpha B_x \quad (27)$$

In the foregoing, the results of studies on the relation between $-\partial B_z/\partial x$ and $B_x$ are described; similarly, this holds true for the relation between $-\partial B_z/\partial y$ and $B_y$, and approximate equation (28) of equation (22') is deemed to be satisfied.

$$\partial B_z/\partial y = -2\alpha B_y \quad (28)$$

Hereinafter, the procedure for determining an isomagnetic field map by estimating tangential components $B_x$ and $B_y$ from the measured normal component $B_z$ on the assumption that $B_x$ is proportional to $-\partial B_z/\partial x$ and $B_y$ is proportional to $-\partial B_z/\partial y$ pursuant to equations (27) and (28) will be described in greater detail.

When a magnetic field component $B_z(x, y, t)$ normal to the surface of a living body is detected, the differential value $\partial B_z(x, y, t)/\partial x$ in x direction of the $B_z(x, y, t)$ and the differential value $\partial B_z(x, y, t)/\partial y$ in y direction of the $B_z(x, y, t)$ are determined and the root $S(x, y, t)$ of square sum of the differential values is determined as indicated by equation (33).

$$S(x, y, t) = \sqrt{[\{\partial B_z(x, y, t)/\partial x\}^2 + \{\partial B_z(x, y, t)/\partial y\}^2]} \quad (33)$$

Subsequently, a waveform $St(x, y, t)$ at each point $(x, y)$ is integrated over a desired time interval to determine an integral value $I_2(x, y)$ pursuant to equation (34), and then an isointegral map for connecting points at which integral values $I_2(x, y)$ at the respective points $(x, y)$ are equal to each other is obtained through interpolation and extrapolation and the isointegral map is displayed on the display screen.

$$I_2(x, y) = \int |S(x, y, t)| dt \quad (34)$$

For example, when the heart is an object to be measured, time intervals during which respective waves Q, R and S are generated, a time interval during which a QRS wave (QRS complex) for generation of Q to S waves is generated and a time interval interval during which a T wave is generated are used for the integration range in equations (4) and (34). Further, a plurality of integration ranges are taken in equations (4) and (34) to determine a plurality of integral values, computation for determining the sum, the difference or the ratio between the integral values is carried out, an isointegral map for connecting points at which the computation results have the same value is determined through interpolation and extrapolation, and the isointegral map is displayed on the display screen. For example, a time interval $T_1$ during which the QRS wave is generated is set as a first integration range and an interval $T_2$ during which the T wave is generated is set as a second integration range, integral values $I_{1,T1}(x, y)$ and $I_{2,T1}(x, y)$ are determined for the time interval $T_1$ pursuant to equation (4) and integral values $I_{1,T2}(x, y)$ and $I_{2,T2}(x, y)$ are determined for the time interval $T_2$ pursuant to equation (34), and sum $I_{sum}(x, y)$ inclusive of isoweight ($w_1$, $W_2$ are weighted values), difference $I_{dif}(x, y)$ or ratio $r(x, y)$ is determined between the integral values $I_{1,T1}(x, y)$ and $I_{1,T2}(x, Y)$ or between the integral values $I_{2,T1}(x, y)$ and $I_{2,T2}(x, y)$ pursuant to equations (35) and (36), equations (37) and (38) or equations (39) and (40).

$$I_{sum}(x, y) = w_1 \times I_{1,T1}(x, y) + w_2 \times I_{1,T2}(x, y) \quad (35)$$

$$I_{sum}(x, y) = w_1 \times I_{2,T1}(x, y) + w_2 \times I_{2,T2}(x, y) \quad (36)$$

$$I_{dif}(x, y) = w_2 \times I_{1,T2}(x, y) - w_1 \times I_{1,T1}(x, y) \quad (37)$$

$$I_{dif}(x, y) = w_2 \times I_{2,T2}(x, y) - w_1 \times I_{2,T1}(x, y) \quad (38)$$

$$r(x, y) = I_{1,T1}(x, y)/I_{1,T2}(x, y) \quad (39)$$

$$r(x, y) = I_{2,T1}(x, y)/I_{2,T2}(x, y) \quad (40)$$

The results of operations pursuant to equations (35) and (36), equations (37) and (38) and equations (39) and (40) suppress irregularities in the isointegral map due to the individual differences, and abnormalities of living body function due to diseases can be detected.

With the isointegral map obtained in the present invention, states of living body portions can be grasped by using a number of maps which is far smaller than the number of maps required in the prior art, without analyzing biophenomena by the use of many maps which are, required in the prior arts, which indicate states of living body portions at respective time points. Since the peak position in the isointegral map obtained by using the tangential component (equation (4)) or the normal component (equation (34)) of a biomagnetic field coincides with a portion in a living body through which a large amount of current flows, from the isointegral map, portions in the living body through which flow a large amount of current within a desired time interval can be decided. The biomagnetic field distribution differs greatly individual by individual, but according to the present invention, the integral value over a desired time interval obtained from a waveform representing a temporal change of a component in each direction of the biomagnetic field is used, and therefore, a more quantitative biomagnetic field distribution can be displayed by using a smaller number of maps, and disease and abnormality of each individual can be grasped objectively and quantitatively.

Further, in the present invention, an isomagnetic field map equivalent to the conventional isomagnetic field map based on $B_{xy}$ (equation (2)) can be obtained by measuring only the normal component $B_z$ without measuring tangential components $B_x$ and $B_y$ through vector measurement. With the conventional isomagnetic field map obtained directly from the normal component $B_z$, a plurality of current sources are difficult to discriminate, but in the isomagnetic field map of the present invention, the peak pattern appears immediately above the current source as in the case of the conventional isomagnetic field map based on $B_{xy}$, and as a result a plurality of current sources in the living body can be observed directly, and the inverse problem of analyzing the position and magnitude of the plurality of current sources can be solved with ease.

To summarize the present invention, reference is made to FIG. 7. More particularly, a biomagnetic field measuring apparatus of the present invention for measuring biomagnetic field distribution inside a shield room 1 has a plurality of fluxmeters, each including a superconducting quantum interference device (SQUID), and operative to detect a biomagnetic field generated from a living body 2 in the form of a signal, an operation processing unit 8 for performing the operation processing of the signal, and a display unit for displaying results of the operation processing. The fluxmeters detect a temporal change of a normal magnetic field component representing a component of the biomagnetic field in a first direction which is normal to the surface of the living body, and the operation processing means performs computation for determining a temporal change of a value proportional to a root of square sum of differential values of the normal magnetic field component in second and third directions which cross the first direction and computation for determining an integral value of the temporal change over a predetermined time interval, and the display means displays the integral value. Since the quantitative biomagnetic field distribution is displayed by using a small number of maps, disease and abnormality of each individual can be grasped objectively and quantitatively.

Further, in the present invention, an isomagnetic field map equivalent to the conventional isomagnetic field map based on $B_{xy}$ (equation (3)) can be obtained by measuring only the normal component $B_z$ without measuring the tangential components $B_x$ and $B_y$ through vector measurement and, by setting the number and position of peaks in a pattern of the obtained isomagnetic field map to the initial condition, the inverse problem of analyzing the position and magnitude of the current source in the living body can be solved with ease.

detected within the time interval during which the QRS complex of cardiac magnetic waveform of the healthy person appears in an embodiment of the present invention.

Figure 17:
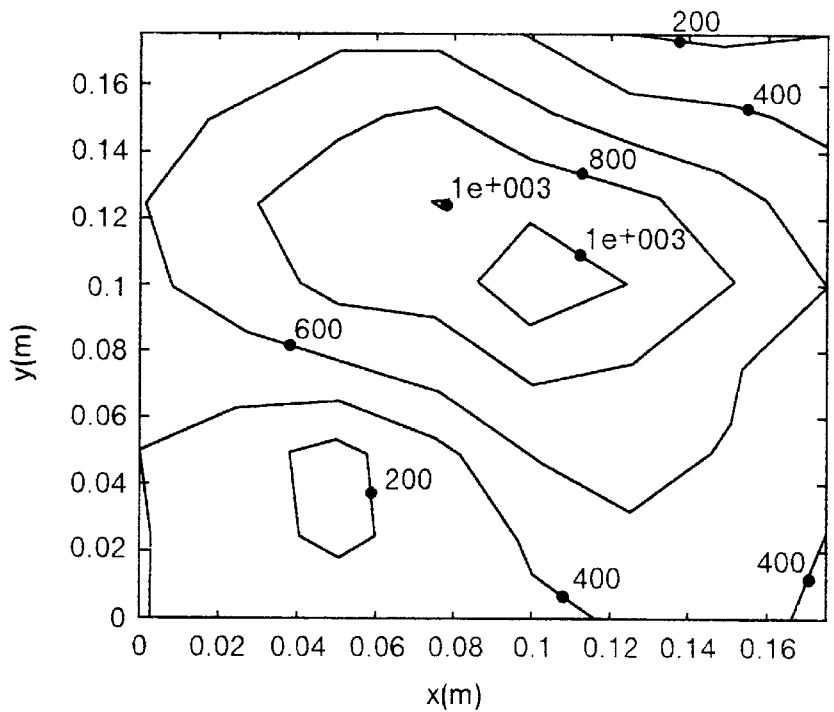

FIG. 17 is an isointegral map obtained from two tangential components detected within a time interval during which a T wave of cardiac magnetic waveform of the healthy person appears in an embodiment of the present invention.

Figure 15:
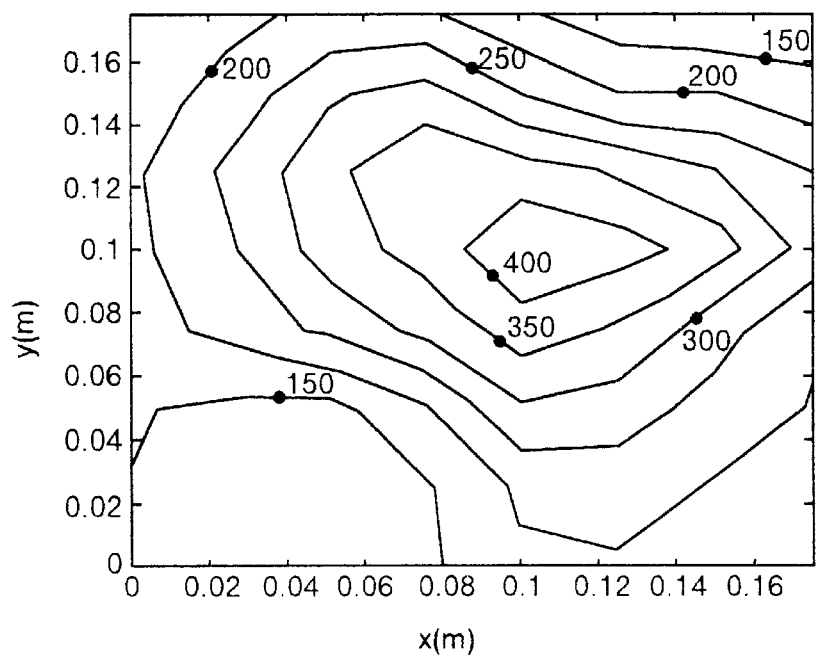
FIG. 15 is an isointegral map obtained from two tangential components detected within a time zone during which a QRS wave (QRS complex) of cardiac magnetic waveform of a healthy person appears in an embodiment of the present invention.
Figure 18:
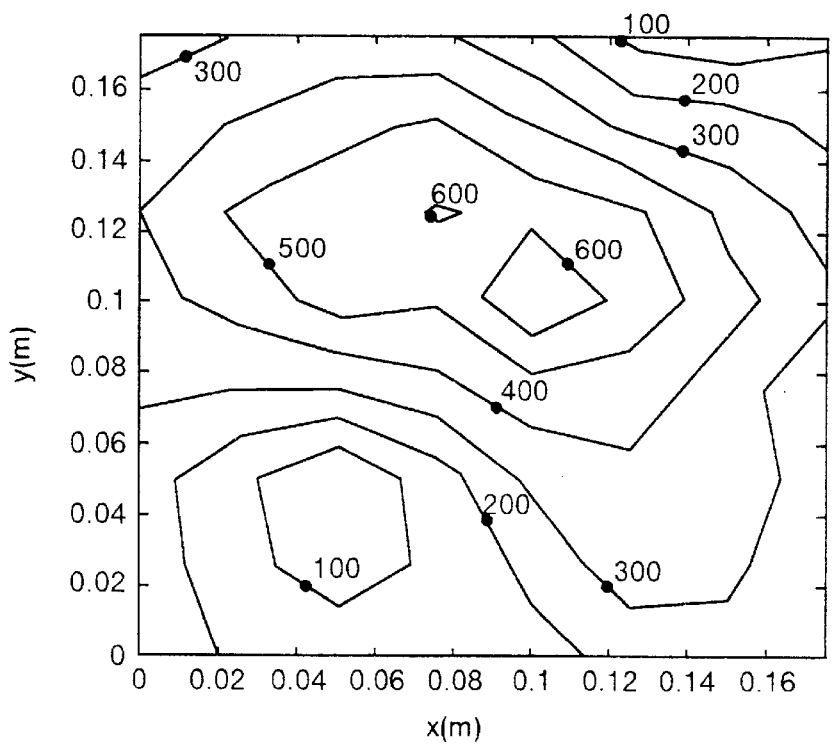

FIG. 18 is a map indicative of the difference obtained by subtracting the isointegral map shown in FIG. 15 from the isointegral map shown in FIG. 17 in an embodiment of the present invention.

Figure 19:
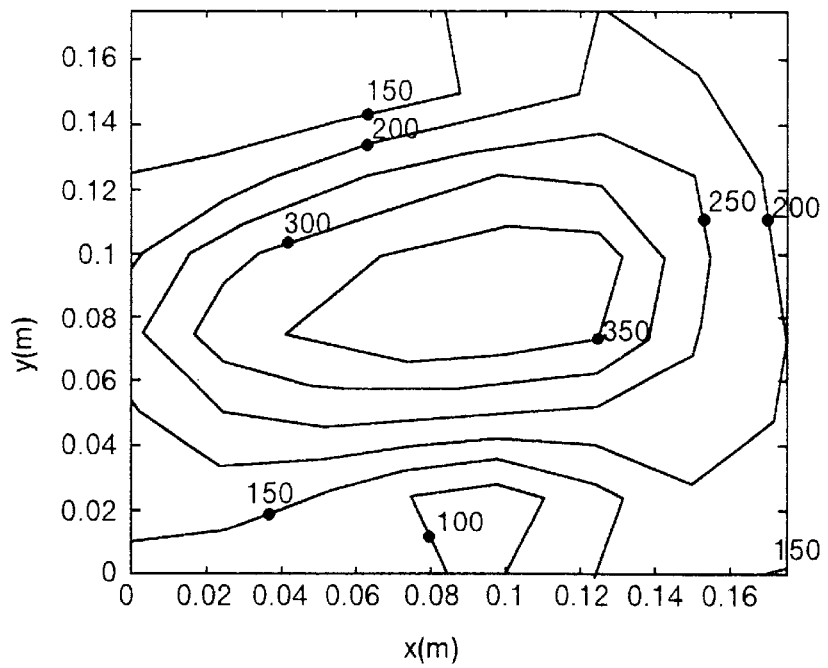

FIG. 19 is an isointegral map obtained from two tangential components detected within a time interval during which a QRS complex of cardiac magnetic waveform of a patient of myocardial infarction appears in an embodiment of the present invention.

Figure 20:
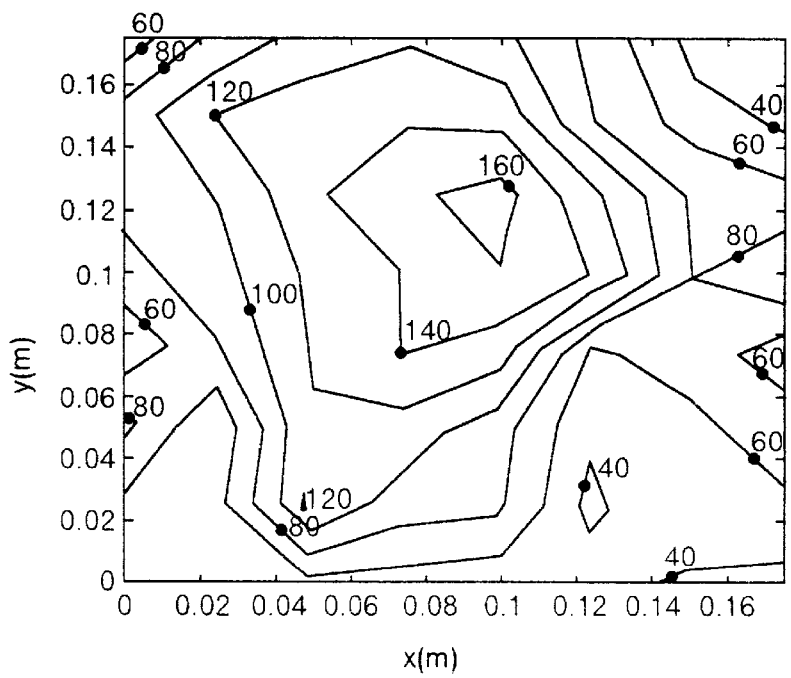

FIG. 20 is an isointegral map obtained from two tangential components detected within a time interval during which a T wave of cardiac magnetic waveform of the patient of myocardial infarction appears in an embodiment of the present invention.

Figure 21:
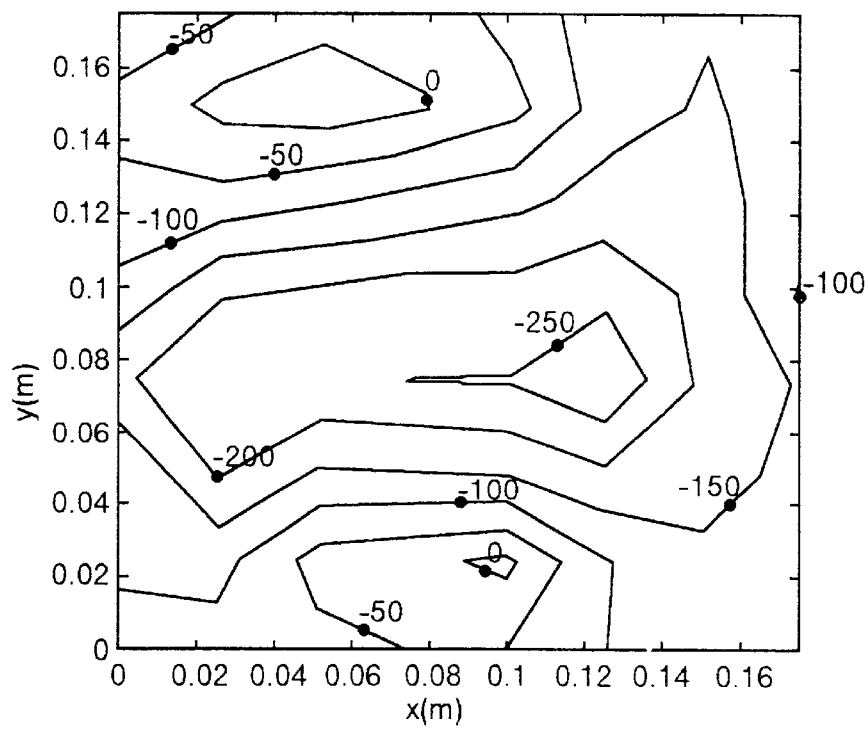
Figure 22:
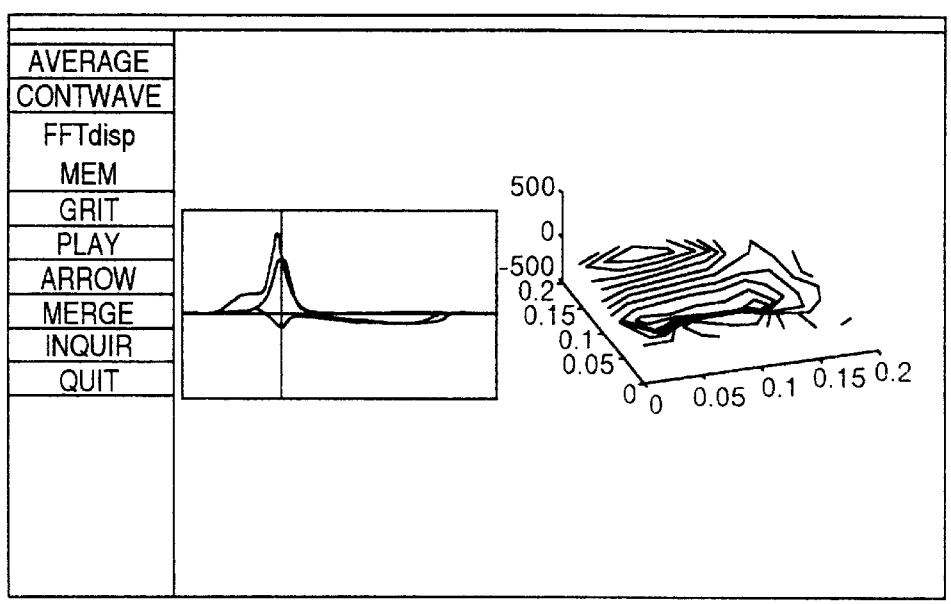

FIG. 21 is a map obtained by subtracting the isointegral map shown in FIG. 19 from the isointegral map shown in FIG. 20 in an embodiment of the present invention FIG. 22 is a diagram showing an example of an output picture on a personal computer of the biomagnetic field measuring apparatus for cardiac magnetic field measurement practicing the present invention.

Figure 23:
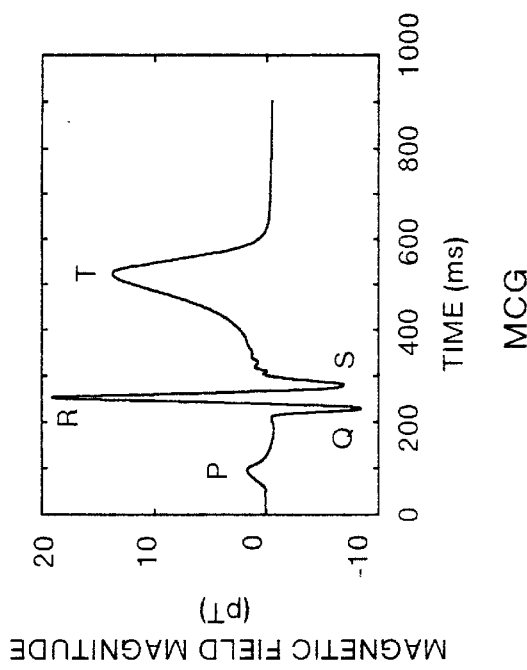
Figure 23:
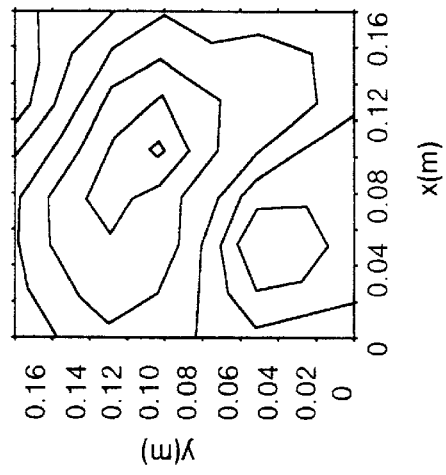
Figure 23:
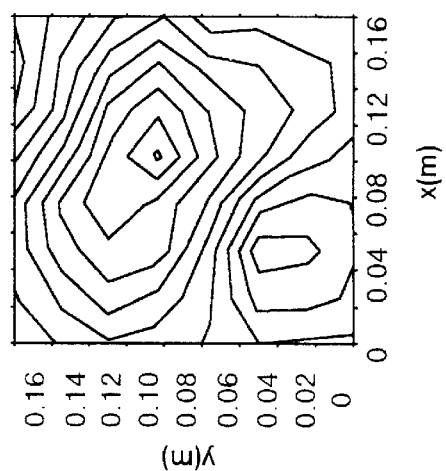
Figure 23:
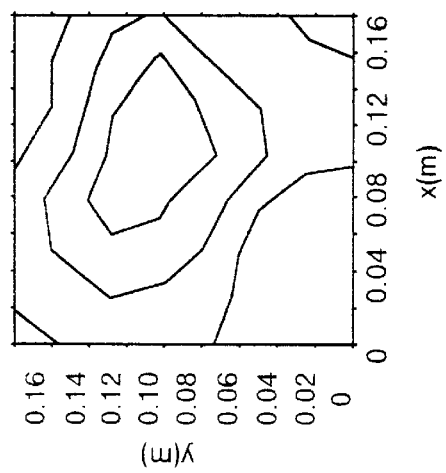

FIG. 23 is a diagram showing examples of processed images displayed on the display of the biomagnetic field measuring apparatus of the present invention.

Figure 24A:
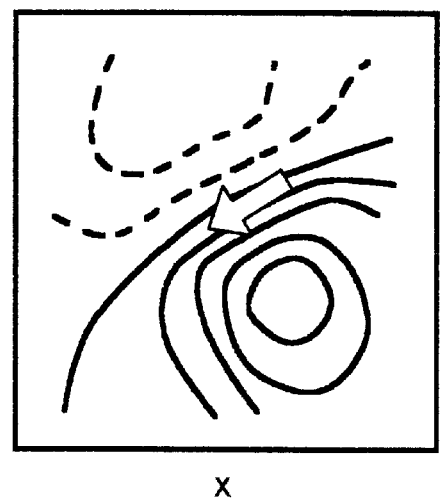
Figure 24B:
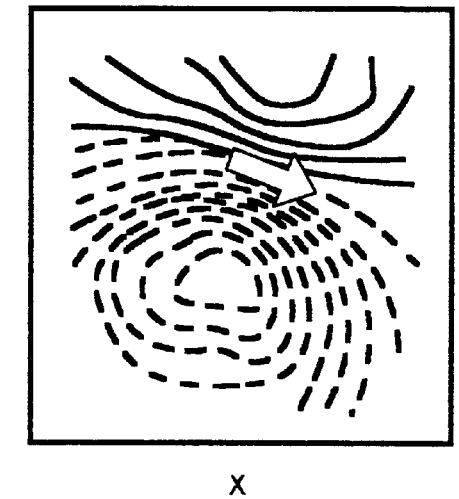
Figure 24C:
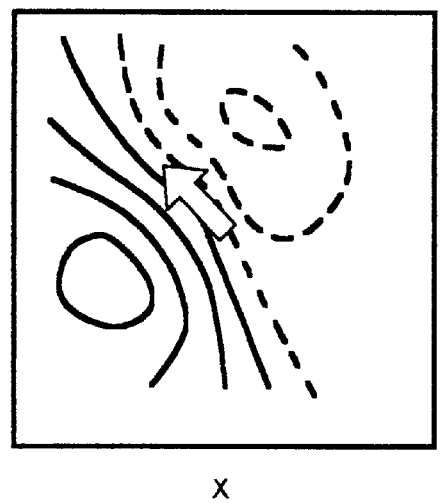

FIGS. 24A, 24B and 24C are isomagnetic field maps at the time that extreme values of Q wave, R wave and S wave of magnetocardiogram (MCG) obtained by measuring normal component $B_z$ in accordance with the conventional method appear.

Figure 25A:
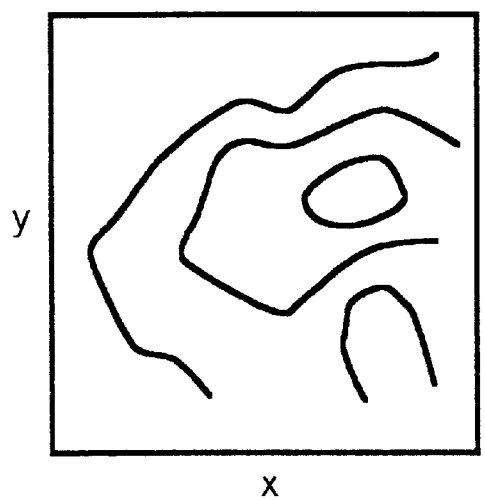
Figure 25B:
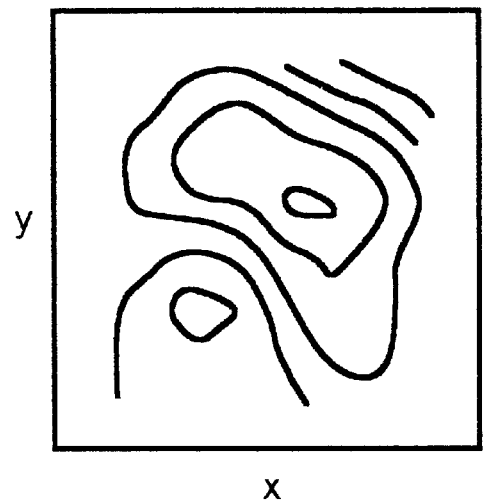
Figure 25C:
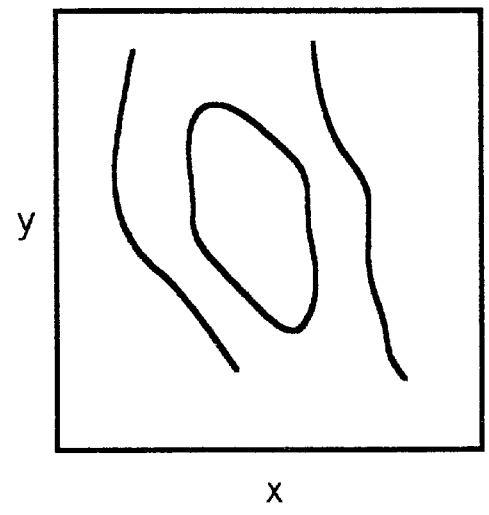

FIGS. 25A, 25B and 25C are isomagnetic field maps of $B_{xy}$ obtained by measuring tangential components $B_x$ and $B_y$ of a magnetic field from the heart and synthesizing the tangential components at the time that extreme values of Q wave. R wave and S wave appear in an embodiment of the present invention.

Figure 26A:
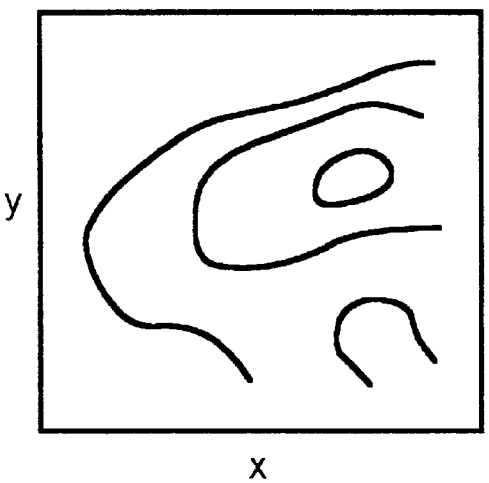
Figure 26B:
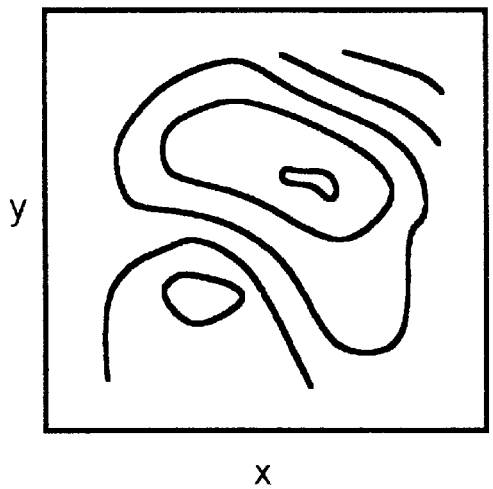
Figure 26C:
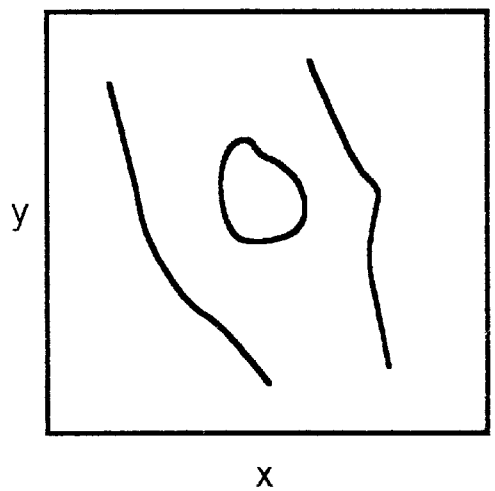

FIGS. 26A, 26B and 26C are isomagnetic field maps at respective time points obtained pursuant to equations (43) and (44) by using isomagnetic map data of normal component $B_z$ at the time that the extreme values of Q, R and S waves shown in FIGS. 24A, 24B and 24C appear in an embodiment of the present invention.

Figure 27:
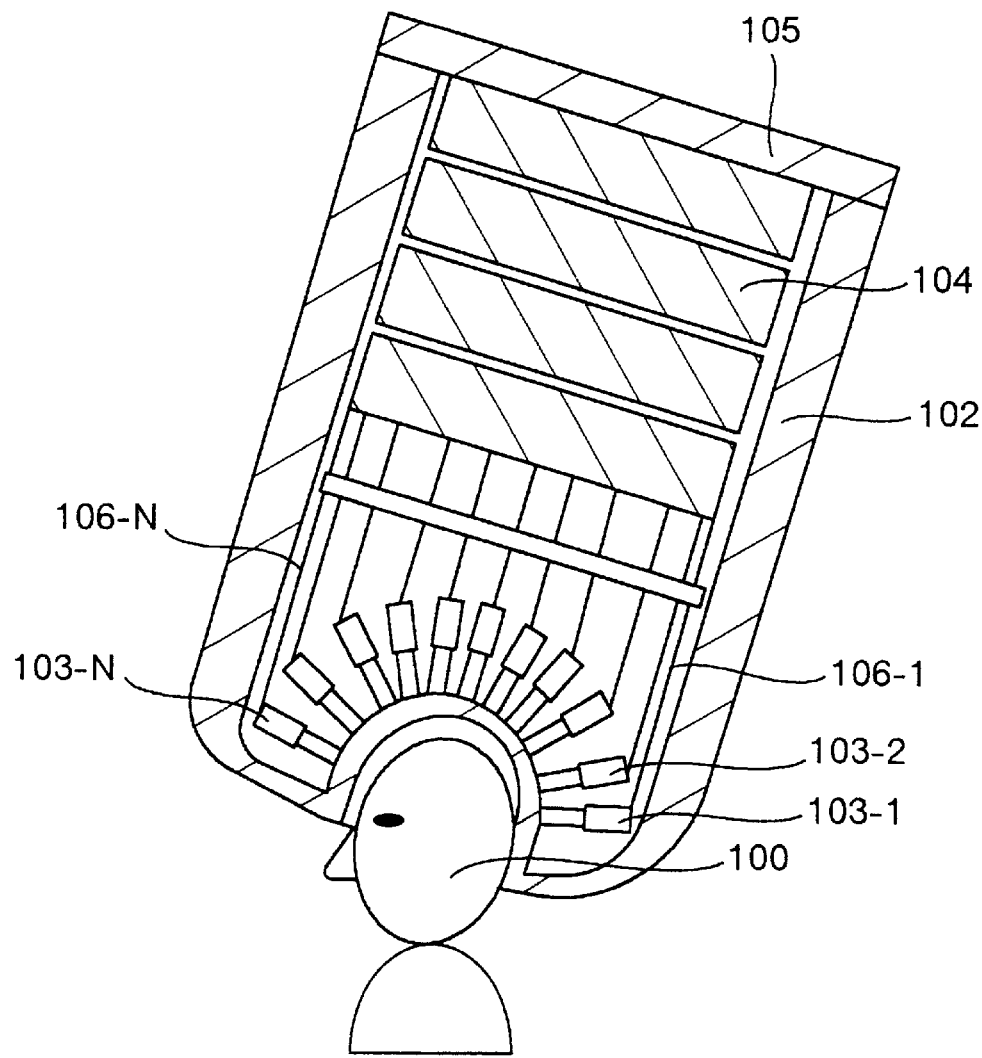

FIG. 27 is a sectional view showing part off the internal construction of a dewar for encephalic magnetic field measurement of a magnetocephalogram (MEG) system which measures an encephalic magnetic field.

Figure 28:
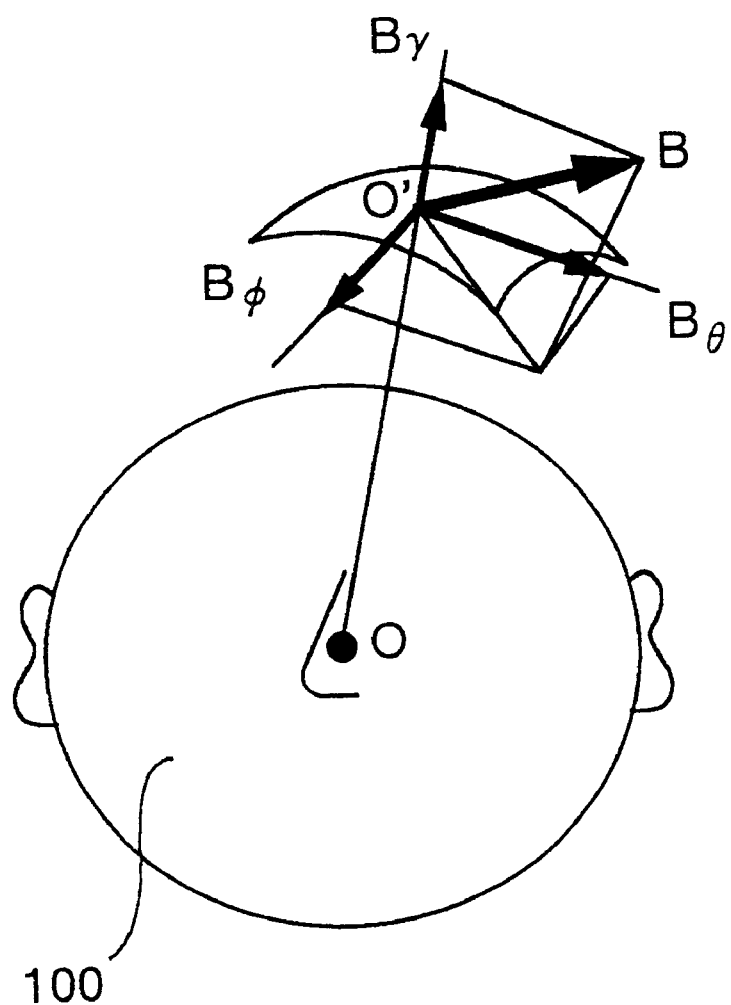

FIG. 28 is a diagram for explaining the relation between a magnetic field component measurable by the MEG system shown in FIG. 27 and the head.

Figure 29A:
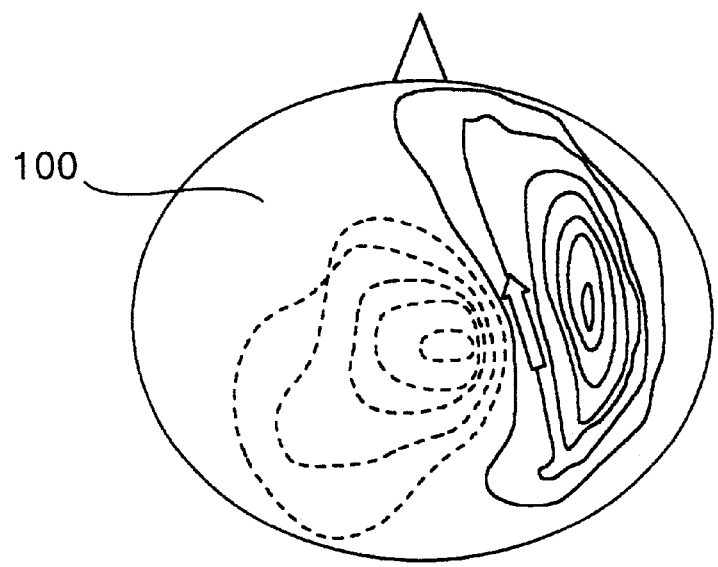
Figure 29B:
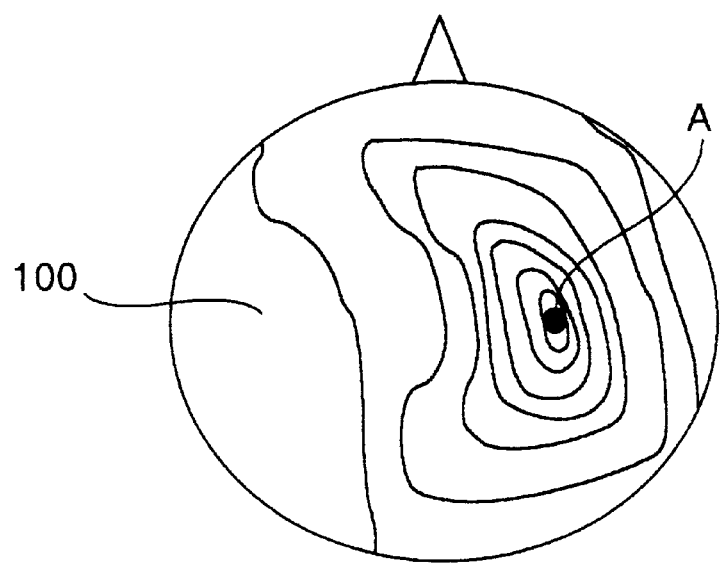

FIGS. 29A and 29B are diagrams showing examples of isomagnetic field maps obtained with the MEG system shown in FIG. 27.

DESCRIPTION OF THE PREFERRED EMBODIMENTS

As a coordinate system in biomagnetic field measurement, the Cartesian coordinate system (x, y, z) where magnetic field components are $B_x$, $B_y$ or $B_z$ and the polar coordinate system (r, θ, φ) is used. When an object to be measured is the heart or the like, the Cartesian coordinate system (x, y, z) having its xy plane corresponding to the wall of the chest is used. When an object to be measured is the brain or the like, the polar coordinate system (r, θ, φ) where magnetic field components are $B_r$, $B_θ$ and $B_φ$, is used because the head has the shape approximating a sphere. In the present embodiment, a magnetic field component normal to the surface of a living body (normal component) is designated by $B_z$ or $B_r$ and components parallel to the living body surface (tangential components) are designated by $B_x$ and $B_y$ or $B_θ$ and $B_φ$. Hereinafter, the present embodiment will be described using the Cartesian coordinate system (x, y, z) but when the polar coordinate system (r, θ, φ) is used, $B_r$, $B_θ$ and $B_φ$ may be read in place of $B_z$, $B_x$ and $B_y$.

Figure 1:
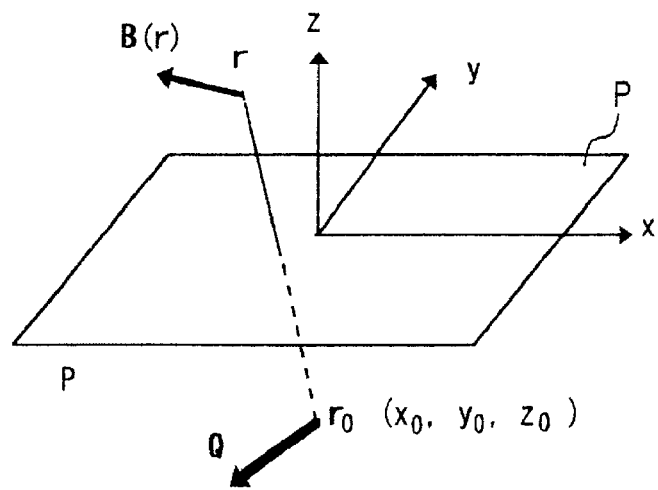
FIG. 1 is a diagram for explaining analysis of the generation of a cardiac magnetic field by using a model of a magnetic field which is generated from a current dipole in a horizontally layered conductor.
Figure 2:
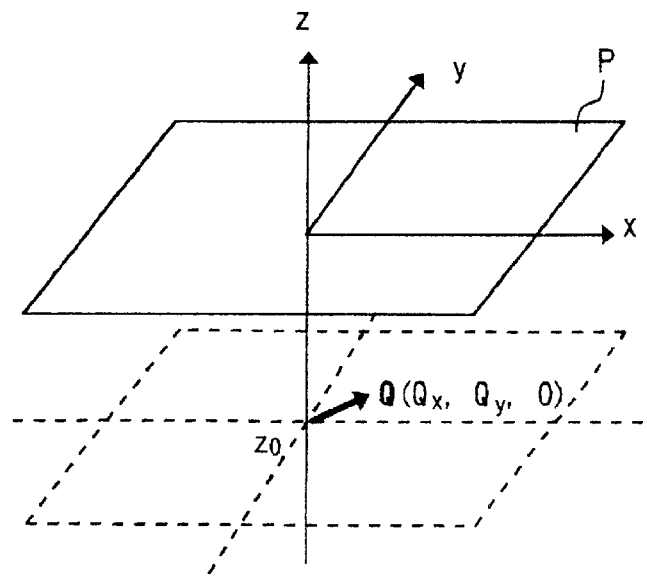
FIG. 2 is a diagram schematically showing the position of a moment of a current dipole existing inside the horizontally layered conductor in the present invention.
Figure 3:
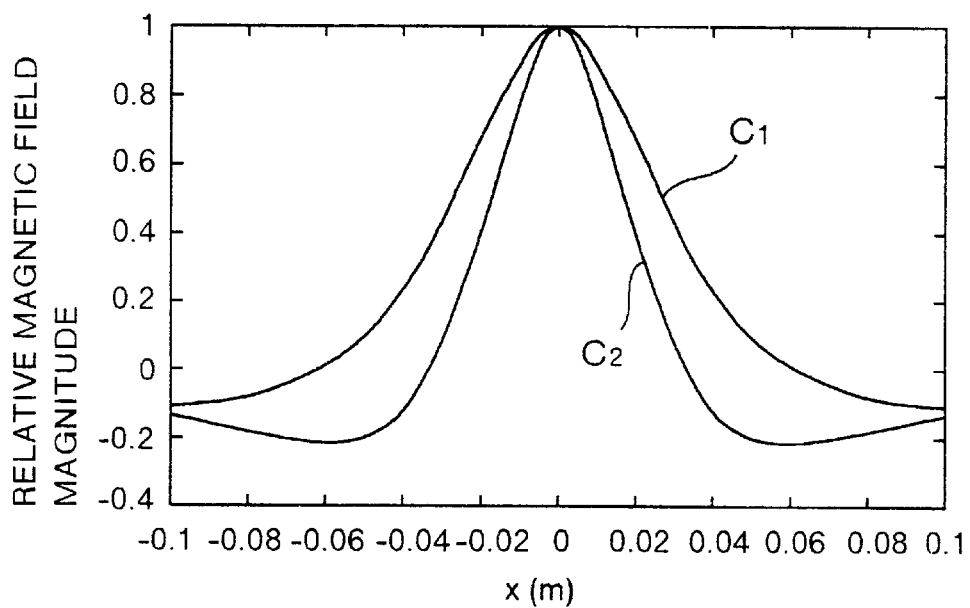
FIG. 3 is a graph showing relative magnetic field magnitude curves $C_1$ and $C_2$ obtained by normalizing $B_x$ and $-\partial B_z/\partial x$ on the horizontally layered conductor by their maximum values in the present invention.
Figure 4:
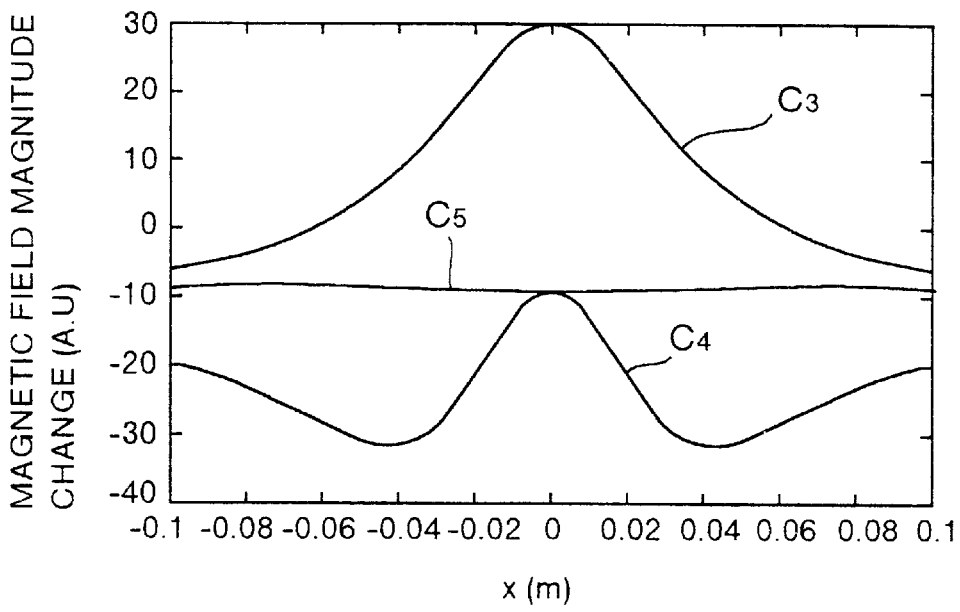
FIG. 4 is a graph showing magnetic field magnitude curves $C_3$, $C_4$ and $C_5$ representative of the first, second and third terms in $-\partial B_z(x, 0)/\partial x$.
Figure 5:
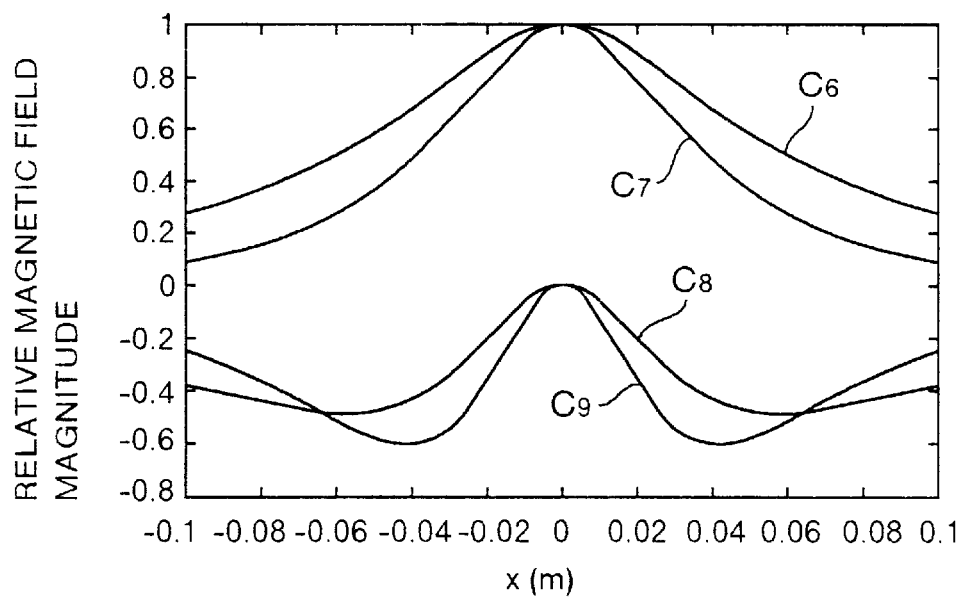
FIG. 5 is a graph showing relative magnetic field magnitude curves $C_6$, $C_7$, $C_8$ and $C_9$ obtained by normalizing the first and second terms of each of the $B_x$ and $\partial B_z/\partial x$ and then comparing the normalized values in the present invention.
Figure 6:
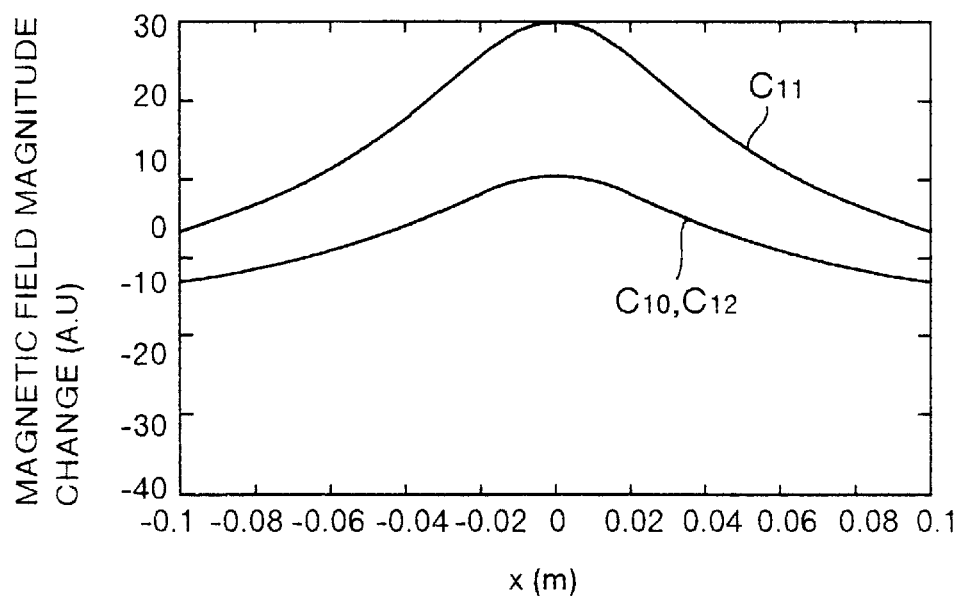
FIG. 6 is a graph showing relative magnetic field magnitude curves $C_{10}$, $C_{11}$ and $C_{12}$ representative of $\alpha=(\nabla K)_z/K$, {first term of $-\partial B_z(x, 0)/\partial x$}/{first term of $B_x(x, 0)$} and {second term of $-\partial B_z(x, 0)/\partial x$}/second term of $B_x(x, 0)$}, respectively, in the present invention.
Figure 7:
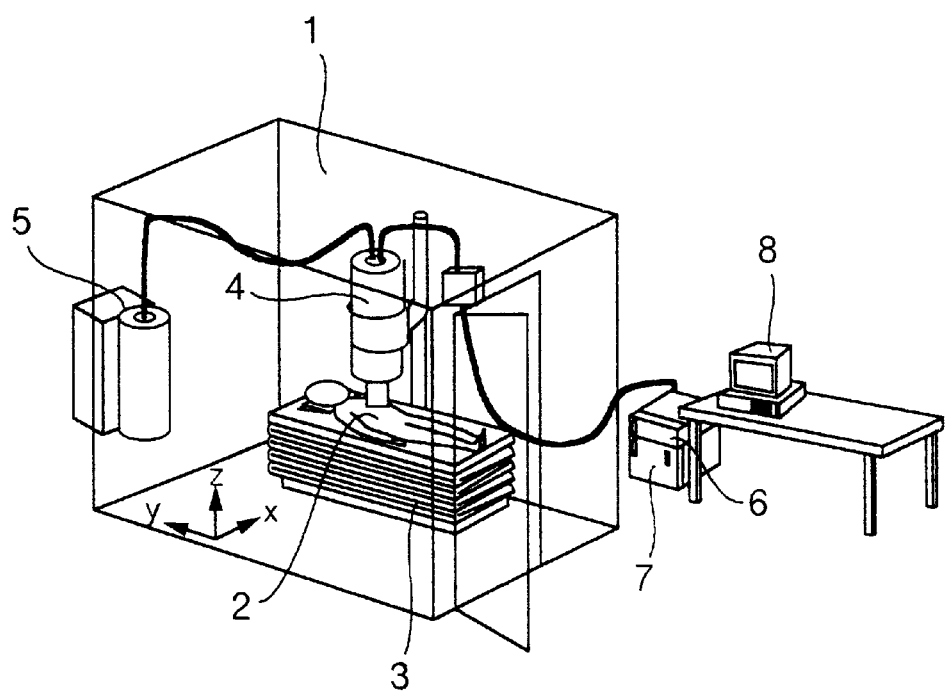
FIG. 7 is a perspective view showing the schematic construction of a biomagnetic field measuring apparatus for cardiac magnetic field measurement practicing the present invention.

FIG. 7 shows the schematic construction of a biomagnetic field measuring apparatus practicing the present invention. The biomagnetic field measuring apparatus for cardiac magnetic field measurement uses a plurality of magnetic field sensors each including a superconducting quantum interference device (SQUID). For elimination of the influence of environmental magnetic field noise, the cardiac magnetic field measurement is carried out inside a magnetically shielded room 1. An object 2 to be inspected lies on a bed 3 to undergo measurement (the Cartesian coordinate system (x, y, z) as shown in FIG. 1 is set so that its xy plane may coincide with the surface of the bed). A dewar 4 accommodating a plurality of magnetic field sensors each comprised of an integrality of a SQUID and a detection coil connected thereto and being filled with liquid He is disposed above the chest of the inspected object 2. The liquid He is replenished continuously by means of an automatic He introducing device 5 disposed externally of the magnetically shielded room 1.

An output of the magnetic field sensor is supplied to a flux locked loop (FLL) circuit 6 which delivers a voltage proportional to the magnitude of a magnetic field detected by the detection coil. The FFL circuit cancels a change in biomagnetic field inputted to the SQUID through a feedback coil in order to keep the output of the SQUID constant. By converting current flowing through the feedback coil into voltage, a voltage output proportional to a change in biomagnetic field signal can be obtained. The voltage output is amplified by an amplifier (not shown), its frequency band is selected by a filter circuit 7 and the resulting signal is subjected to AD conversion by means of an AD converter (not shown) so as to be fetched into a computer 8. In the computer 8, various kinds of operation processing are executed, and the results of the operation processing are displayed on the display and delivered to a printer.

Figure 8:
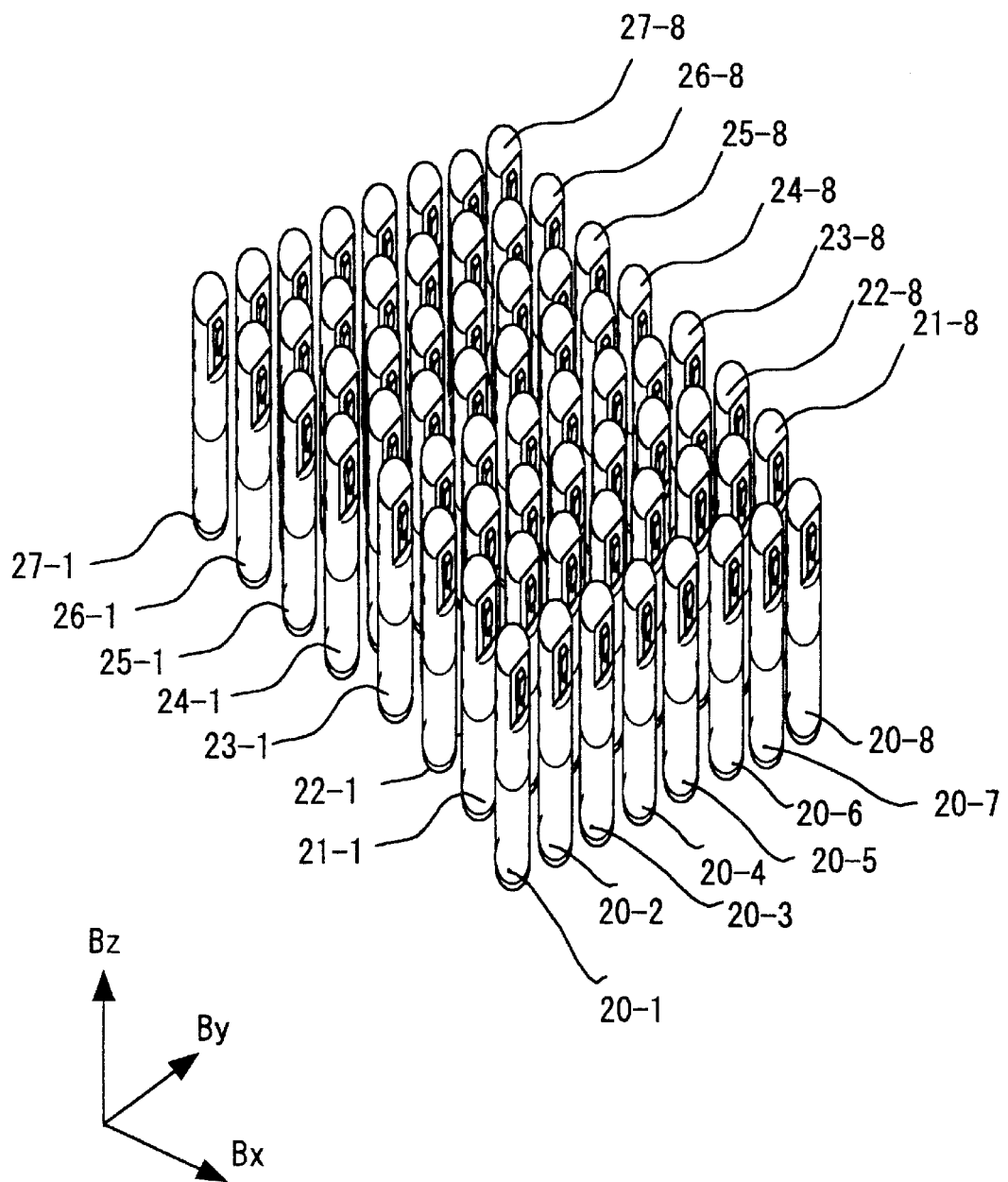
FIG. 8 is a perspective view showing the arrangement of magnetic field sensors in the biomagnetic field measuring apparatus for cardiac magnetic field measurement practicing the present invention.

As detection coils for detecting tangential components of a magnetic field, two coils having their coil planes oriented to x and y directions, respectively, are used. As a coil for detecting a normal component of the magnetic field, a coil oriented to z direction is used. The arrangement of these magnetic field sensors (20-1 to 20-8, 21-1 to 21-8, 22-1 to 22-8, 23-1 to 23-8, 24-1 to 24-8, 25-1 to 25-8, 26-1 to 26-8 and 27-1 to 27-8) is shown in FIG. 8. The magnetic field sensors stand uprightly inside the dewar from the bottom thereof and the respective sensors are spaced apart equidistantly in x and y directions in order that a distance-dependent change of the magnetic field can be caught accurately. Here, the inter-sensor distance is 25 mm and the number of sensors is 8×8 =64 (channels).

Figure 9:
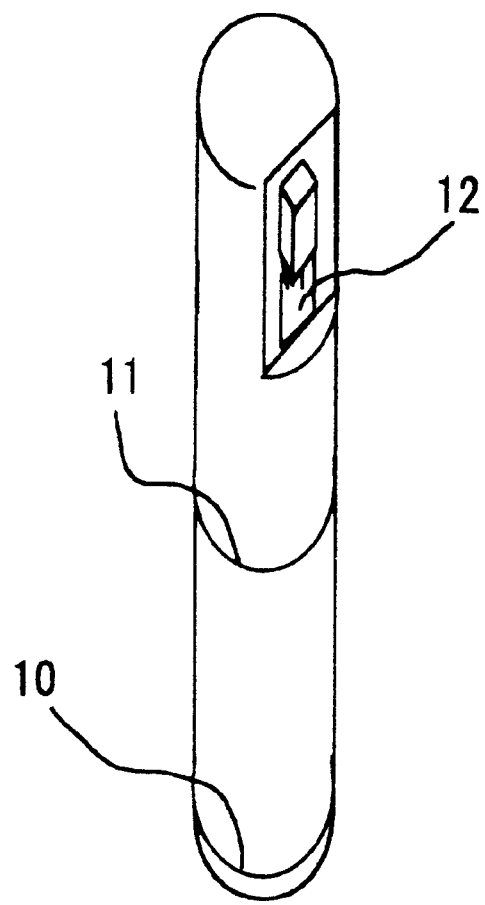
FIG. 9 is a perspective view showing the construction of a single magnetic field sensor for detecting a normal component of a magnetic field in the biomagnetic field measuring apparatus for cardiac magnetic field measurement practicing the present invention.
Figure 9:
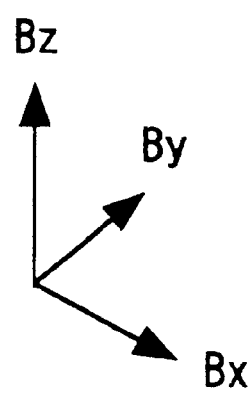
Figure 10:
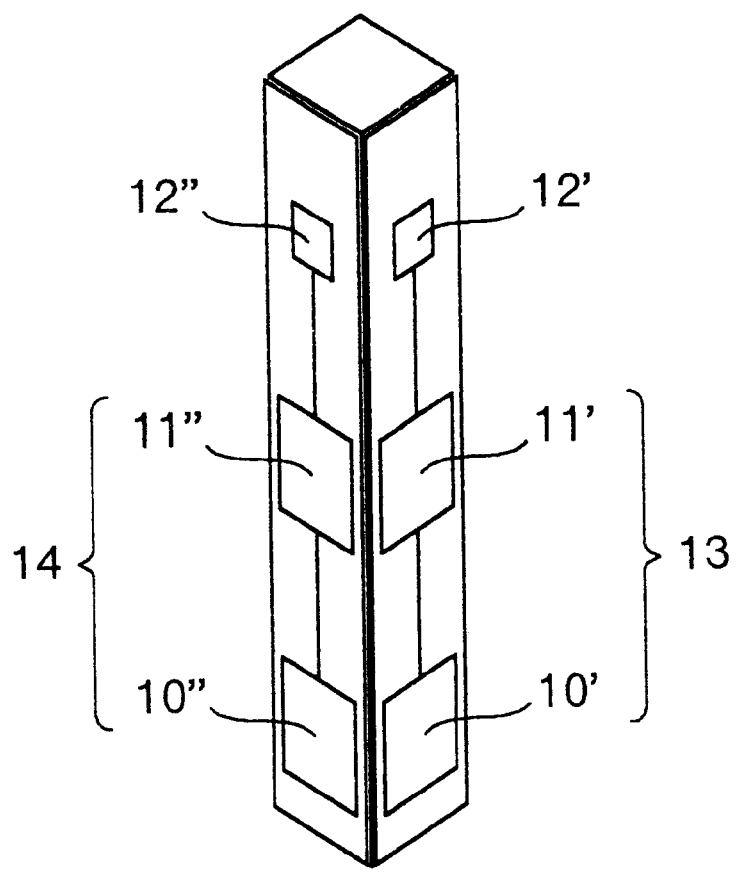
FIG. 10 is a perspective view showing the construction of a single magnetic field sensor for detecting a tangential component of the magnetic field in the biomagnetic field measuring apparatus for cardiac magnetic field measurement practicing the present invention.

One of the magnetic field sensors arranged in the manner as above is schematically shown in FIG. 9 or FIG. 10. A magnetic field sensor shown in FIG. 9 is adapted to detect a normal component $B_z$ normal to the body surface and has a coil formed of a superconducting conductor (Nb—Ti conductor) and having its plane oriented to z direction. In this coil, two reverse coils, of which one is a detection coil 10 close to the living body and the other is a reference coil 11 remote from the living body adapted to eliminate external magnetic field noise, are combined to form a first order gradiometer. Exemplarily, the coil diameter is 20 mm and the base line between the coils is 50 mm. The external magnetic field noise is generated from a signal source remote from the living body and can be detected equally by the detection and reference coils. On the other hand, a signal from the living body is detected more strongly by the detection coil 10 close to the living body than by the reference coil 11. Therefore, the detection coil 10 can afford to detect both the signal and the noise but the reference coil 11 can detect only the noise. Accordingly, by taking in the difference between magnetic fields captured by the two coils, measurement can be carried out with a high S/N ratio.

The first order gradiometer is connected to an input coil of a SQUID 12 through a superconducting wiring line of a package substrate packaging the SQUID 12 to transmit to the SQUID a biomagnetic field detected by the detection coil.

The schematic construction of a magnetic field sensor for detecting tangential components $B_x$ and $B_y$ of the biomagnetic field is illustrated in FIG. 10. The magnetic field sensor uses planar coils, of which detection coil 10' and reference coil 11' are arranged on one plane and detection coil 10" and reference coil 11" are arranged on another plane. The coil size is 20 mm×20 mm and the base line is 50 mm. Like the coil for normal component, these coils are connected to package substrates of SQUID's 12' and 12". A sensor for magnetic field in x direction, generally designated by reference numeral 13, and a sensor for magnetic field in y direction, generally designated by reference numeral 14, are stuck to two mutually orthogonal surfaces of a support in the form of a prism to form a magnetic field sensor which can detect x and y components. The prisms are arranged in an array as shown in FIG. 8.

Figure 11:
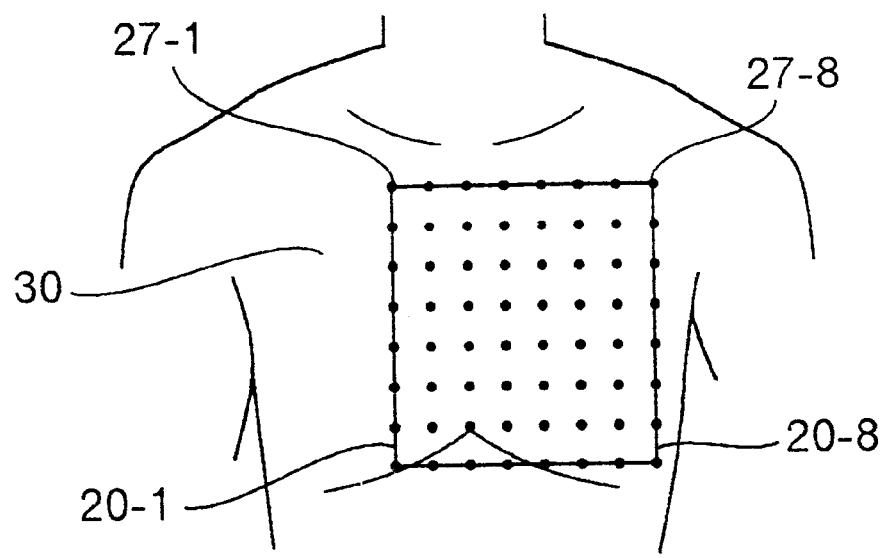
FIG. 11 is a diagram showing the positional relation between the arrangement of magnetic field sensors and the chest of a body in the biomagnetic field measuring apparatus for cardiac magnetic field measurement practicing the present invention.
Figure 11:
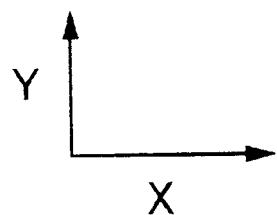

The dewar incorporating the magnetic field sensors is disposed above the chest of the inspected object lying on the bed to detect a magnetic field generated from the heart. Here, the transverse direction of the body is defined as x direction and the longitudinal direction of the body is defined as y direction. The positional relation between the arrangement of the magnetic field sensors (20-1 to 20-8, 21-1 to 21-8, 22-1 to 22-8, 23-1 to 23-8, 24-1 to 24-8, 25-1 to 25-8, 26-1 to 26-8 and 27-1 to 27-8) and the chest 30 is shown in FIG. 11. Biomagnetic field signals detected under the above positional relationship are shown in FIGS. 12A, 12B and 12C.

Figure 12A:
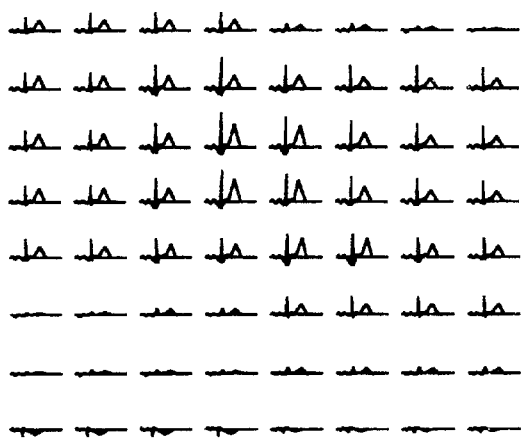
FIGS. 12A, 12B and 12C are diagrams showing temporal waveforms of respective components of a magnetic field generated from the heart of a healthy person and measured at positions of the respective magnetic field sensors in an embodiment of the present invention.
Figure 12B:
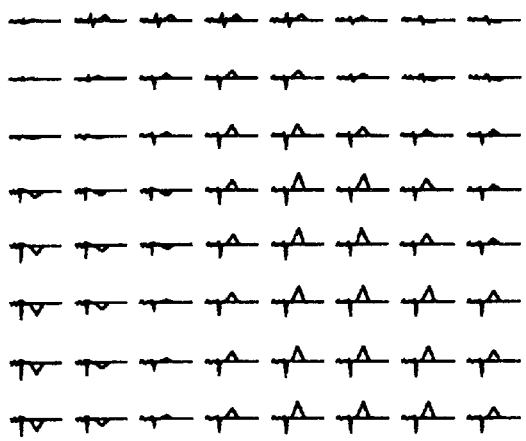
Figure 12C:
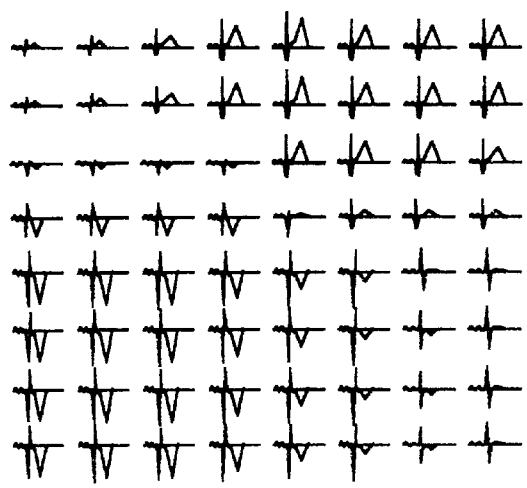

FIGS. 12A, 12B and 12C show temporal changes of a magnetic field generated from the heart of a healthy person which are detected by the respective magnetic field sensors (8×8 magnetic field sensors arranged in array), where in each figure, abscissa of 64 waveforms represents time axis and ordinate represents detected magnetic field magnitude. Specifically, FIG. 12A shows time (abscissa)-dependent changes of tangential component $B_x$, FIG. 12B shows time-dependent changes of tangential component $B_y$ and FIG. 12C shows time-dependent changes of normal component $B_z$, where illustrated values of the respective components are normalized by an absolute value of signal magnitude obtained from a channel which delivers a maximum signal magnitude.

Figure 13:
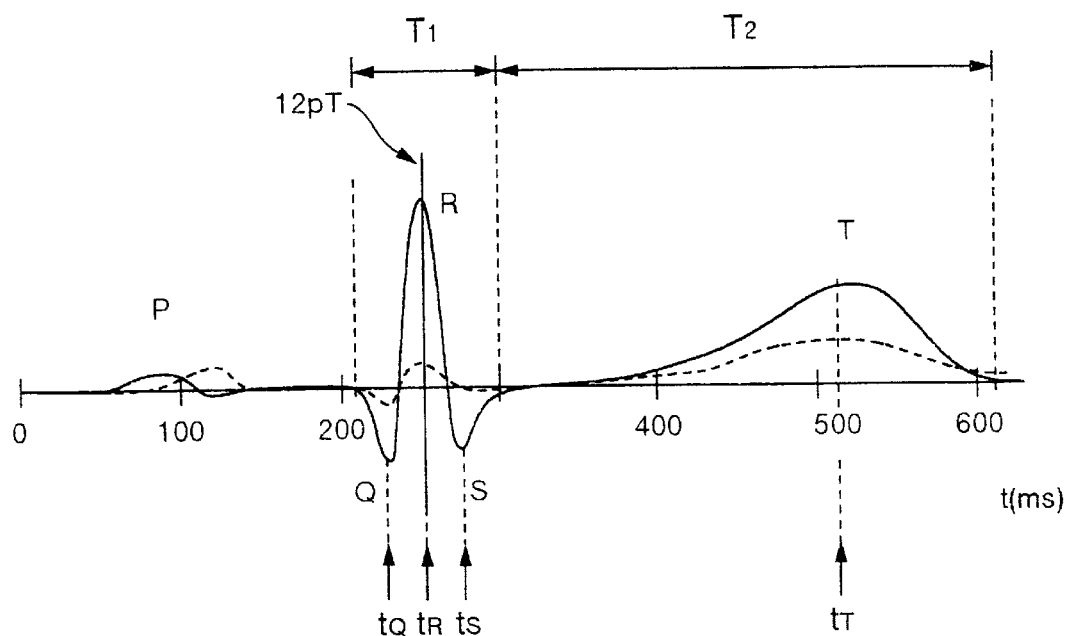
FIG. 13 is a temporal waveform (time chart) showing tangential components ($B_x$) in two specified channels measured for the healthy person in an embodiment of the present invention.

Temporal waveforms (time charts) of tangential component ($B_x$) shown at solid and dotted curves in FIG. 13 are obtained through two specified channels when a healthy person is measured. Time points at which peaks (extreme values) of Q, R and S waves are given within a time interval $T_1$ for appearance of a QRS wave resulting from depolarization of the ventricle of the heart are indicated by $t_Q$, $t_R$ and $t_S$, respectively, in FIG. 13. Further, a time interval for appearance of a T wave indicative of the process of repolarization of the heart is indicated by $T_2$ and a time point at which a peak (extreme value) is given is indicated by $t_T$.

In FIG. 13, P wave indicates excitation (depolarization) of the atrium, QRS wave consisting of Q, R and S waves indicates excitation (depolarization) of the ventricle and T wave is a gradual deflection which indicates repolarization of the myocardium. The depolarization represents a process in which excitation initially spreads in the muscle and the repolarization represents a process in which the excited muscle returns to a still state.

Figure 14A:
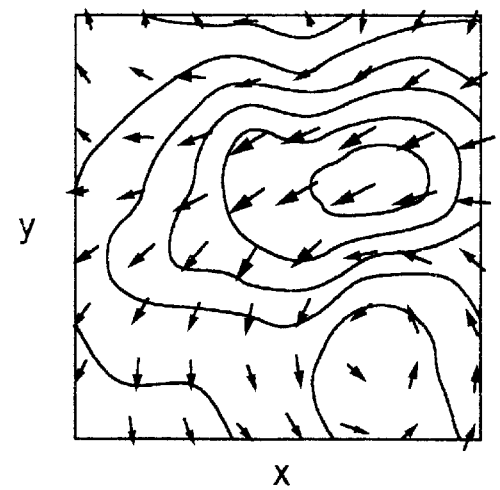
FIGS. 14A, 14B and 14C are an isomagnetic field map at the moment of a peak of Q wave, an isomagnetic field map at the moment of a peak of R wave and an isomagnetic field map at the moment of a peak of S wave, respectively, these maps being obtained from a cardiac magnetic waveform of a healthy person for whom tangential components $B_x$ and $B_y$ of a magnetic field are measured in an embodiment of the present invention.
Figure 14B:
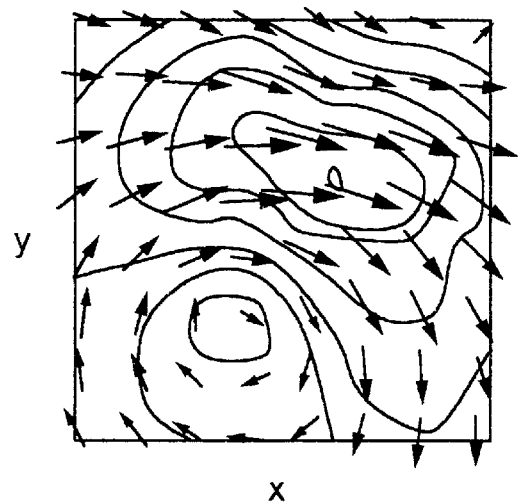
Figure 14C:
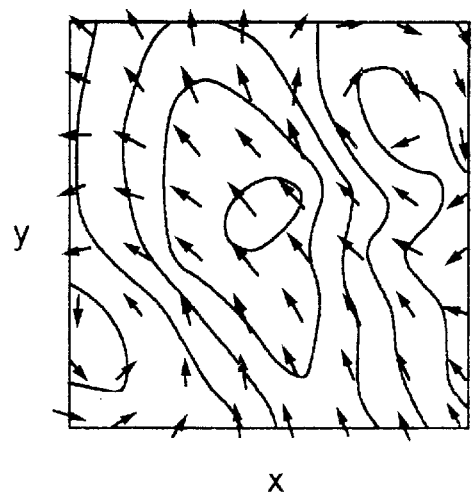

FIGS. 14A, 14B and 14C show isomagnetic field maps for connecting points at which magnitudes of cardiac magnetic fields are equal to each other at time points $t_Q$, $t_R$ and $t_S$, respectively. Each of the FIGS. 14A, 14B and 14C shows a two-dimensional vector magnitude distribution indicated by $|B_{xy}(x, y, t)|$ of equation (4) and obtained by synthesizing tangential components $B_x$ and $B_y$ measured at 64 points. Further, in each of the FIGS. 14A, 14B and 14C, arrows show two-dimensional vectors on the assumption that current sources at 64 measuring points generate magnetic fields at the respective measuring points. By using the current vectors, the direction and distribution of currents in the heart can be presumed. In each of the FIGS. 14A, 14B and 14C, abscissa x and ordinate y indicate coordinates at which the magnetic field sensors are located. Current flowing in the heart flows in the right-down direction in the ventricular septum at the moment of the peak of the Q wave as shown in FIG. 14A, a large amount of current flows obliquely downwards in the whole of the left ventricle at the moment of the peak of the R wave as shown in FIG. 14B and current flows obliquely upwards toward the ventricle base at the moment of the peak of the S wave, demonstrating that the depolarization process of the ventricle ends. It will therefore be seen that the isomagnetic field maps of FIGS. 14A, 14B and 14C make it possible to visualize active portions and current direction in the heart at respective time points.

FIG. 15 shows an isointegral map obtained by integrating two-dimensional vector magnitudes $|B_{xy}(x, y, t)|$ at respective points (x, y), obtained from two tangential components $B_x$ and $B_y$ detected within the time interval $T_1$ during which the QRS wave covering Q to S waves of the cardiac magnetic waveform appears, pursuant to equation (4) and connecting points at which integral values are equal to each other. In FIG. 15, x axis and y axis represent coordinates of the magnetic field sensors disposed on the body surface and numerical values described near black circles associated with the respective curves of the isointegral map indicate integral values owned by the corresponding curves. It will be seen from FIG. 15 that most of currents flowing in the myocardium within the time interval of QRS wave take place in the left ventricle in which the myocardium is thick and the peak position in the isointegral map exactly corresponds to a portion at which the amount of current flowing in the heart is large.

Figure 16:
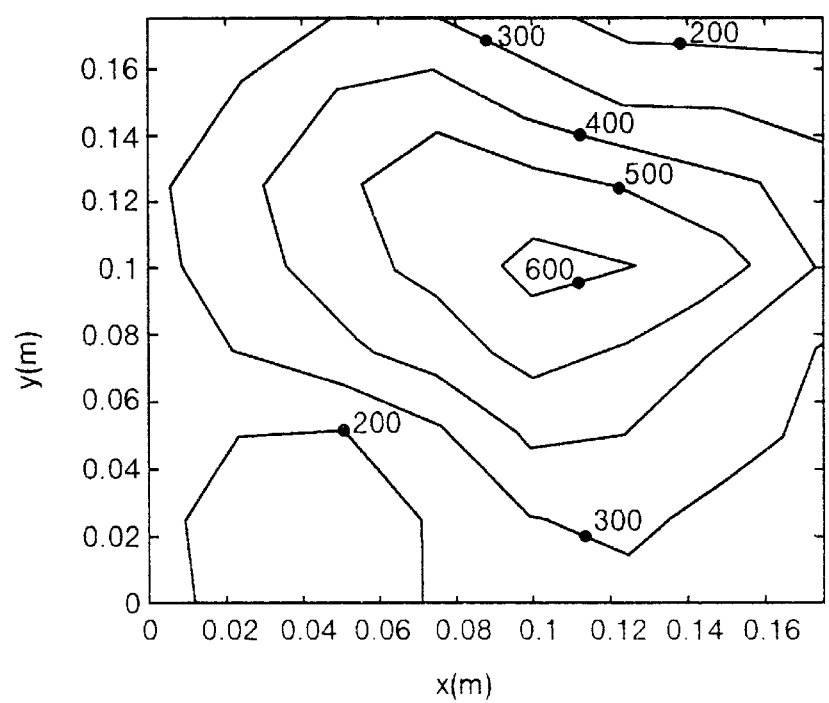
FIG. 16 is an isointegral map $$\left(\sqrt{\left(\frac{\partial B_z}{\partial x}\right)^2 + \left(\frac{\partial B_z}{\partial y}\right)^2}\right) \text{ obtained from a normal component}$$

FIG. 16 shows an isointegral map obtained by measuring normal components $B_z$ at respective points (x, y) in connection with the same healthy person for whom data of FIG. 15 is determined from FIGS. 12A, 12B and 12C, determining roots S(x, y) pursuant to equation (33), integrating the resulting roots over the time interval $T_1$ of the QRS wave pursuant co equation (34) and connecting points at which integral values are equal to each other. In FIGS. 16 to 21, x axis and y axis represent positional coordinates (in a unit of m) of the magnetic field sensors disposed on the body surface. In FIGS. 16 to 21, numerical values described near black circles associated with curves represent integral values owned by the corresponding curves.

It has been found that a pattern of the isointegral map of FIG. 15 determined from the magnetic field tangential components $B_x$ and $B_y$ coincides with a pattern of the isointegral map of FIG. 16 determined from the magnetic field normal component $B_z$. The coincidence means that equations (6) and (7) or equations (27) and (28) are satisfied substantially by experimental data.

FIG. 17 shows an isointegral map obtained by integrating two-dimensional vector magnitudes $|B_{xy}(x, y)|$ at respective points (x, y), obtained from two tangential components $B_x$ and $B_y$ detected within the time zone $T_2$ of the T wave in connection with the same healthy person for whom FIG. 15 is determined, pursuant to equation (4) and connecting points at which the integral values are equal to each other.

FIG. 18 shows a contour line map which represents the difference pursuant to equation (37) between the integral value over the time interval $T_2$ pursuant to equation (4) and the integral value over the time interval $T_1$ for generation of the QRS wave pursuant to equation (4). In other words, the map of FIG. 18 is obtained by subtracting the isointegral map shown in FIG. 15 from that shown in FIG. 17. The time interval $T_2$ of T wave is longer than the time interval $T_1$ of QRS wave. The pattern in FIG. 17 resembles that in FIG. 15. Therefore, the contour line map shown in FIG. 18 has positive values as a whole. Numerical values described near black circles associated with curves in FIGS. 17 and 18 each represent the aforementioned difference value between integral values owned by the corresponding curve.

Next, results of cardiac magnetic field measurement in a patient of myocardial infarction are shown in FIGS. 19, 20 and 21. FIG. 19 shows an isointegral map obtained for the time interval $T_1$ of QRS wave similarly to FIG. 15, FIG. 20 shows an isointegral map obtained for the time interval $T_2$ of T wave similarly to FIG. 17 and FIG. 21 shows a contour line map obtained similarly to FIG. 18 to indicate the difference pursuant to equation (35) between the integral value over the time interval $T_2$ of T wave pursuant co equation (4) and the integral value over the time interval $T_1$ of QRS wave pursuant to equation (4). In other words, FIG. 21 is a map obtained by subtracting the isointegral map shown in FIG. 19 from that shown in FIG. 20. Numerical values described near black circles associated with curves in FIGS. 19 and 20 represent integral values owned by the corresponding curves and numerical values described near black circles associated with curves in FIG. 21 represent the difference value between the integral values owned by the corresponding curve.

The isointegral map for the time interval $T_1$ shown in FIG. 19 has a pattern which slightly differs from those of the isointegral maps shown in FIGS. 15 and 16, indicating that a large amount of current has passed through the left ventricle. But the isointegral map for the time interval $T_2$ shown in FIG. 20 has a pattern which differs from that of the isointegral man for the time interval $T_1$ shown in FIG. 19, clearly indicating that the pattern of the amount of current flowing through the heart within the time interval $T_1$ greatly differs from that within the time interval $T_2$ owing to myocardial infarction. Further, the contour line map shown in FIG. 21 has negative values as a whole and greatly differs from the contour line map of the healthy person shown in FIG. 18 having positive values as a whole, clearly indicating that in the patient of myocardial infarction, the current flowing through the heart within the time interval $T_2$ suffers from infliction.

As described above, by imaging the magnetic field magnitude of the heart within the time intervals $T_1$ and $T_2$, the healthy state can be discriminated non-invasively with ease from the abnormal state (for example, the myocardial infarction condition, cardiac ischemic condition or the like) within a short period of time of less than one minute without inflicting pain on the patient. In other words, early finding or estimating of a diseased portion can be ensured without solving the inverse problem.

FIG. 22 shows an example of a processed image on the screen of the computer of the biomagnetic field measuring apparatus. The screen is of the multi-window type and individual processed images can be displayed on respective windows. While in FIGS. 15 to 21 numerical values are described in association with individual curves to clarify the level of the magnetic field magnitude and integral value, coloring is effected on the display in accordance with the level of the contour line to provide a three-dimensional color display. At the same time, the time chart (magnetocardiogram) as shown in FIG. 13 as well as an electrocardiogram can also be displayed to permit systematic analysis of the heart disease.

FIG. 23 shows examples of processed images displayed on the display of the biomagnetic field measuring apparatus of the present invention. In FIG. 23, MCG depicts an example of magnetocardiogram, QRS depicts an example of a first isointegral map obtained pursuant to equation (34) when the integration range is set to the time interval $T_1$ for generation of the QRS wave, T depicts an example of a second isointegral map obtained pursuant to equation (34) when the integration range is set to the time interval $T_2$ for generation of the T wave, and (T-QRS) depicts an example of the difference between the first and second isointegral maps.

In equations (4) and (34), $I_1(x, y)$ and $I_2(x, y)$ can be determined by a simplified method substituting for the integration. More particularly, $I_1(x, y)$ and $I_2(x, y)$ are determined from the following equations (41) to (44) and then, equations (35) to (40) are applied. When tangential components (components parallel to the surface of living body) $B_x(x, y, t)$ and $B_y(x, y, t)$ of a magnetic field generated from the living body are measured (where in the Cartesian coordinate system (x, y, z), the plane parallel to the body surface is the xy plane and the axis perpendicular to the body surface is z), the two-dimensional vector magnitude $|B_{xy}(x, y)|$, where $|\ |$ represents absolute value, is determined from a root of square sum of the tangential components $B_x$ and $B_y$ pursuant to equation (41).

$$|B_{xy}(x, y, t_0)|=\sqrt{\{(B_x(x, y, t_0))^2+(B_y(x, y, t_0))^2\}} \qquad (41)$$

Subsequently, for respective points (x, y), values $I_1(x, y)$ of a waveform $|B_{xy}(x, y, t_0)|$ at a desired time point are determined pursuant to equation (42), an isomagnetic field map for connecting points at which values of $I_1(x, y)$ at the respective points (x ,y) are equal to each other is obtained through interpolation and extrapolation, and the isomagnetic field map is displayed on the display screen.

$$I_1(x, y)=|B_{xy}(x, y, t_0)| \qquad (42)$$

When a magnetic component $B_z(x, y, t)$ normal to the living body surface is measured, a differential value $\partial B_z(x, y, t_0)/\partial x$ in x direction of the vertical magnetic component $B_z$ and a differential value $\partial B_z(x, y, t_0)/\partial y$ in y direction of the $B_z(x, y, t_0)$ are determined and as shown in equation (43), a root $S(x, y, t)$ of the square sum is determined.

$$S(x, y, t_0)=\sqrt{[\{x, y, t_0)/\partial x\}^2+\{\partial B_z(x, y, t_0)/\partial y\}^2]} \qquad (43)$$

Subsequently, for the respective points (x, y), values $I_2(x, y)$ of a waveform $S(x, y, t_0)$ at a desired time point are determined pursuant to equation (44), an isomagnetic field map for connecting points at which values of $I_2(x, y)$ are equal co each ocher at the respective points (x, y) is determined through interpolation and extrapolation, and the isomagnetic field map is displayed on the display screen.

$$I_2(x, y) = |S(x, y, t_0)| dt \quad (44)$$

For example, when the heart is an object to be measured, to in equations (41) to (44) is the time that the maximum value of each wave Q, R or S is given in response to contraction of the ventricle. Further, in equations (41) to (44), a plurality of time points $t_0$ are set, computation for determining the sum, the difference or the ratio between a plurality of determined values is carried out, an isomagnetic field map for connecting points at which computation results are equal to each other is determined through interpolation and extrapolation, and the isomagnetic field map is displayed on the display screen. In this manner, too, substantially the same results as those obtained by the previously-described method using equations (4) and (34) can be obtained.

Isomagnetic field maps at the time that the extreme values of Q, R and S waves in a magnetocardiogram of patient X obtained by measuring a normal component Bz in accordance with the conventional method are illustrated in FIGS. 24A, 24B and 24C. In FIGS. 24A, 24B and 24C, dotted lines indicate an isomagnetic map of a negative magnetic field, solid line indicates an isomagnetic map of a positive magnetic field and a blank arrow indicates the magnitude and direction of a current dipole. In illustrations of the isomagnetic field maps of FIGS. 24A, 24B and 24C, the blank arrow is superimposed at the position of a current dipole when a single current source existing in the heart is supposed. At the time that the extreme value of Q wave appears, the current flows in a right-down direction in the ventricular septum as shown in FIG. 24A. A large amount of current flows obliquely downwards in the whole of the left ventricle as shown in FIG. 24B at the time that the extreme value of R wave appears and the current flows obliquely upwards toward the ventricle base as shown in FIG. 24C at the time that the extreme value of S wave appears, indicating that the depolarization process in the ventricle ends.

Isomagnetic field maps obtained by measuring tangential components $B_x$ and $B_y$ of a magnetic field generated from the heart of the aforementioned patient X and synthesizing the tangential components pursuant to equations (41) and (42) at the time that the extreme value of each of the Q, R and S waves appears are illustrated in FIGS. 25A, 25B and 25C.

A pattern of FIG. 25A substantially coincides with that of FIG. 24A, a pattern of FIG. 25B substantially coincides with that of FIG. 24B and a pattern of FIG. 25C substantially coincides with that of FIG. 24C. But, in the pattern of FIG. 25B obtained at the time that the extreme value of R wave appears, the myocardium acts in a wide region to ensure that a plurality of current sources, not clear in the pattern of FIG. 24B obtained a: the moment of the appearance of the extreme value of R wave, can be discriminated easily, making it possible to know that one current source exists in the left direction and the other current source exists downwards.

Isomagnetic field maps at the time that the respective extreme values of Q, R and S waves appear, which are obtained pursuant to equations (43) and (44) by using isomagnetic map data pieces of the normal component $B_z$ at the moment of the appearance of the respective extreme values of Q, R and S waves, are illustrated in FIGS. 26A, 26B and 26C. From the results shown in FIGS. 26A, 26B and 26C, a plurality of current sources, which are hardly discriminated by the use of the isomagnetic field maps of normal component $B_z$ shown in FIGS. 24A, 24B and 24C or the arrow map based on equation (1), can be discriminated. It will be appreciated that patterns of FIGS. 26A, 26B and 26C are equivalent to those (isomagnetic field maps of $B_{xy}$ obtained by synthesizing the tangential components $B_x$ and $B_y$) shown in FIGS. 25A, 25B and 25C. This means that equations (6) and (7) or equations (27) and (28) are satisfied to substantially by practical experimental data.

In each of the FIGS. 24A to 26C, abscissa x and ordinate y represent positional coordinates of the magnetic field sensors disposed on the living body surface.

While in the foregoing the present invention has been described by way of example of cardiac magnetic field measurement, the present invention can obviously be applied to even encephalic magnetic field measurement for obtaining a magnetoencephalogram (MEG).

FIG. 27 shows, in sectional view form, part of the internal construction of a dewar for encephalic magnetic field measurement of an encephalic magnetic field measuring system for measurement of an encephalic magnetic field. When an encephalic magnetic field is measured, an object to be inspected is the head which differs from the chest by taking the form of a sphere and therefore, as shown in FIG. 27, the bottom surface of a dewar 102 incorporating SQUID fluxmeters 103-1, 103-2, 103-N is made to take the form of a semi-sphere which covers a head 100. The SQUID fluxmeters 103-1, 103-2, . . . , 103-N are disposed radially along the inner surface of the head measuring dewar 102 and the fore end surface (magnetic field measuring surface) of each SQUID fluxmeter is disposed substantially in parallel to the tangential plane of the semi-spherical surface. The radius of the semi-sphere is set on the assumption that the brain of the head is a sphere having its center which substantially coincides with the center of the semi-sphere, amounting up to about 10 cm which permits measurement for even grown-up persons. A thermal radiation shield 104 is arranged inside the head measuring dewar 102 and the top of the head measuring dewar is sealingly closed by a top plate 105. Signals detected by the SQUID fluxmeters 103-1, . . . , 103-N are taken out to the outside of the head measuring dewar through signal lines 106-1, . . . , 106-N.

FIG. 28 is useful to explain the relation between the magnetic component measurable by the encephalic magnetic field measuring system shown in FIG. 27 and the head. The component of an encephalic magnetic field B measurable by a SQUID fluxmeter disposed radially above the head at one of a plurality of positions, O', is a component Br in r direction (normal component) on the polar coordinate system (r, θ, φ) having its origin at O. In FIG. 28, components $B_\theta$ and $B_\phi$ indicate tangential components parallel to the head surface and the origin is the center of a sphere on the assumption that the brain takes the form of the sphere. An electrical stimulation is applied, as a bodily sense, to the right middle finger, the normal component Br is detected by the encephalic magnetic field measuring system shown in FIG. 27 and an isomagnetic field map at the time that a brain wave appearing about 100 msec after the application of the electrical stimulation is maximized is obtained. FIGS. 29A and 29B show examples of the isomagnetic field map obtained with the encephalic magnetic field measuring system shown in FIG. 27. The isomagnetic map of normal component Br shown in FIG. 29A is obtained in accordance with the conventional method and the isomagnetic map of FIG. 29B is obtained by using the following equation (45)

according to the present invention. Like a map depicted on a globe, the isomagnetic field map indicates the magnitude distribution of the encephalic magnetic field depicted on the surface of the sphere approximating the brain.

$$S(\theta,\phi,t) = \sqrt{\{(\partial B_r(t)/\partial\theta)^2 + (\partial B_r(t)/\partial\phi)^2\}} \quad (45)$$

In the isomagnetic field map shown in FIG. 29A, the current dipole when a single current source existing in the brain is supposed is positioned at a blank arrow superimposed on the illustration. In FIG. 29A, dotted lines represent an isomagnetic field map of a negative magnetic field, solid lines represent an isomagnetic field map of a positive magnetic field and the blank arrow indicates the magnitude and direction of a current dipole. It can be directly visualized with ease that the current source (represented by the current dipole indicated by the blank arrow) conventionally presumed on the basis of the isomagnetic field map of normal component Br shown in FIG. 29A takes place in correspondence to a peak position A in the isomagnetic field map shown in FIG. 29B. The other part of the encephalic magnetic field measuring system, which is not shown in FIG. 27, is constructed essentially identically to that of the biomagnetic field measuring apparatus shown in FIG. 7.

As methods of analyzing the magnetic field source by using the isomagnetic field maps concerning cardiac magnetic field and encephalic magnetic field obtained through the various methods of the present invention described so far, various kinds of algorithms for solving the inverse problem are conceivable. In a simplified algorithm used frequently in practical applications, a single or two or so current dipoles are assumed as the magnetic field source, positional coordinates at which these current dipoles exist are supposed desirably as the initial condition, and on the assumption that the current dipoles existing at the individual positional coordinates generate magnetic fields indicated by the Biot-Savart formula, magnetic fields at actual magnetic field measuring points (x, y) are calculated. An evaluation function pursuant to equation (46) which is indicated by the difference between calculated magnetic field $B_c(x, y)$ and actually measured magnetic field $V_m(x, y)$ is calculated where m=1, 2, M and the total number of measuring points at which the magnetic fields are actually measured is represented by M, and the minimum value of evaluation function L is analytically determined by changing the positional coordinates of the individual current dipoles. In equation (46), G represents a constant, $n_s$ represents a unit vector in normal or z direction, and addition symbol Σ represents the addition concerning m=1, 2, M.

$$L = \Sigma\{V_m(x, y) - G([B_c(x, y)] \cdot n_s)\}^2 \quad (46)$$

With the method based on equation (46), however, an instance occurs where the results of magnetic field source analysis do not converge to the minimum value when a wide measuring region of magnetic field is analyzed. In the present invention, the initial conditions for the position and number of dipoles in the course of calculation of the evaluation function L are so predetermined that the peak position in the isomagnetic field map based on equation (3), (33) or (45) is the position of the dipole and the number of peaks in the isomagnetic field map is the number of dipoles. By solving the evaluation function L under the thus predetermined initial conditions, results of the magnetic field source analysis can converge without fail. By designating respective peak positions on the isomagnetic field maps concerning cardiac magnetic field and encephalic magnetic field based on equation (3), (33) or (45), coordinates of the respective peak positions and the number thereof can be inputted automatically, as the initial values, to the apparatus and the evaluation function L can be solved to provide converging results of magnetic field source analysis.

Accordingly, in contrast to the conventional setting of initial values effected in trail and error fashion, the initial values can be determined substantially definitely with ease on the basis of data of the isomagnetic field map obtained as a result of measurement and the inverse problem can be solved efficiently and more accurately.

In each of the figures depicting the isomagnetic field maps used in the foregoing description, the right side of the body is illustrated on the left side of the drawing and the left side of the body is illustrated on the right side of the drawing in accordance with the common rule practiced in the field of medical treatment.

What is claimed is:

1. A biomagnetic field measuring method comprising the steps of:

(1) measuring a magnetic field component ($B_r$ (θ, φ, t)) in an r axis direction of a biomagnetic field generated from a source within a living body by using a plurality of fluxmeters disposed in parallel to a tangential plane of a surface of a semi-sphere, each fluxmeter including a superconducting quantum interference device (SQUID), wherein a radius of said semi-sphere is set on the assumption that a shape of said source is a sphere having a center which coincides with the center of said semi-sphere and coincides with an origin of the polar coordinate system (r, θ, φ), the r axis direction is perpendicular to the surface of said semi-sphere, and tangential components ($B_\theta$ (θ, φ, t), $B_\phi$ (θ, φ, t)) parallel to the surface of said semi-sphere of said biomagnetic field from said source are estimated from said magnetic field component ($B_\theta$ (θ, φ, t)) in the r axis direction;

(2) determining a value proportional to a root of $$S(\theta, \phi, t) = \{(\delta B_r (\theta, \phi, t)/\delta\theta)^2 + (\delta B_r (\theta, \phi, t)/\delta\phi)^2\}$$

from said magnetic field component ($B_r$ (θ, φ, t)) in the r axis direction, and determining an isomagnetic field map obtained by connecting points at which said values proportional to said root are equal to each other; and (3) displaying said isomagnetic field map.

2. A biomagnetic field measuring method comprising the steps of:

(1) measuring a magnetic field component ($B_r$ (θ, φ, t)) in an r axis direction of a biomagnetic field generated from a source within of a living body by using a plurality of fluxmeters disposed in parallel to a tangential plane of a surface of a semi-sphere, each fluxmeter including a superconducting quantum interference device (SQUID), wherein a radius of said semi-sphere is set on the assumption that a shape of said source is a sphere having a center which coincides with the center of said semi-sphere and coincides with an origin of the polar coordinate system (r, θ, φ), the r axis direction is perpendicular to the surface of said semi-sphere, and tangential components ($B_\theta$ (θ, φ, t), $B_\phi$ (θ, φ, t)) parallel to the surface of said semi-sphere of said biomagnetic field from said source are estimated from said magnetic field component ($B_r$ (θ, φ, t)) in the r axis direction;

(2) determining a magnetic wave form expressing a temporal change of a value proportional to a root of $$S(\theta, \phi, t) = \{(\delta B_r (\theta, \phi, t)/\delta\theta)^2 + (\delta B_r (\theta, \phi, t)/\delta\phi)^2\}$$

from said magnetic field component ($B_r(\theta, \phi, t)$) in the r axis direction, integrating said magnetic wave form within a predetermined time interval to determine an integral value, and determining an isointegral map obtained by connecting points at which said integral values are equal to each other; and (3) displaying said isointegral map.

3. A biomagnetic field measuring method comprising the steps of:

(1) measuring a magnetic field component ($B_r(\theta, \phi, t)$) in an r axis direction of a biomagnetic field generated from a source within of a living body by using a plurality of fluxmeters disposed in parallel to a tangential plane of a surface of a semi-sphere, each fluxmeter including a superconducting quantum interference device (SQUID), wherein a radius of said semi-sphere is set on the assumption that a shape of said source is a sphere having a center which coincides with the center of said semi-sphere and coincides with an origin of the polar coordinate system (r, $\theta$, $\phi$), the r axis direction is perpendicular to the surface of said semi-sphere, and tangential components ($B_\theta(\theta, \phi, t)$, $B_\phi(\theta, \phi, t)$) parallel to the surface of said semi-sphere of said biomagnetic field from said source are estimated from said magnetic field component ($B_r(\theta, \phi, t)$) in the r axis direction;

(2) determining a magnetic field component ($B_\theta(\theta, \phi, t)$) in a $\theta$ axis direction from said magnetic field ($B_r(\theta, \phi, t)$) in the r axis direction on the assumption that said magnetic field component ($B_\theta(\theta, \phi, t)$) in the $\theta$ axis direction is proportional to $$\delta B_r(\theta, \phi, t)/\delta\theta,$$

and determining a magnetic field component ($B_\phi(\theta, \phi, t)$) in a $\phi$ axis direction from said magnetic field component ($B_r(\theta, \phi, t)$) in the r axis direction on the assumption that said magnetic field component ($B_\phi(\theta, \phi, t)$) in the $\phi$ axis direction is proportional to $$\delta B_r(\theta, \phi, t))/\delta\phi; \text{ and}$$

(3) determining a magnetic wave form expressing a temporal change of a value proportional to a root of $$S(\theta, \phi, t) = \{(\delta B_r(\theta, \phi, t)/\delta\theta)^2 + (\delta B_r(\theta, \phi, t)/\delta\phi)^2\}$$

from said magnetic field component ($B_r(\theta, \phi, t)$) in the r axis direction.

4. A biomagnetic field measuring method comprising the steps of:

(1) measuring a magnetic field component ($B_r(\theta, \phi, t)$) in an r axis direction of a biomagnetic field generated from a source within a living body by using a plurality of fluxmeters disposed in parallel to a tangential plane of a surface of a semi-sphere, each fluxmeter including a superconducting quantum interference device (SQUID), wherein a radius of said semi-sphere is set on the assumption that a shape of said source is a sphere having a center which coincides with the center of said semi-sphere and coincides with an origin of the polar coordinate system (r, $\theta$, $\phi$), the r axis direction is perpendicular to the surface of said semi-sphere, and tangential components ($B_\theta(\theta, \phi, t)$, $B_\phi(\theta, \phi, t)$) parallel to the surface of said semi-sphere of said biomagnetic field from said source are estimated from said magnetic field component ($B_r(\theta, \phi, t)$) in the r axis direction; and (2) determining a magnetic field ($B_\theta(\theta, \phi, t)$) in a $\theta$ axis direction from said magnetic field component ($B_r(\theta, \phi, t)$) in the r axis direction on the assumption that said magnetic field component $B_\theta(\theta, \phi, t)$) in a $\theta$ axis direction is proportional to $$\delta B_r(\theta, \phi, t))/\delta\theta,$$

and determining a magnetic field component ($B_\phi(\theta, \phi, t)$) in a $\phi$ axis direction from said magnetic field component ($B_r(\theta, \phi, t)$) in the r axis direction on the assumption that said magnetic field component ($B_\phi(\theta, \phi, t)$) in the $\phi$ axis direction is proportional to $$\delta B_r(\theta, \phi, t))/\delta\phi.$$

5. A biomagnetic field measuring apparatus comprising:

a plurality of fluxmeters disposed in parallel to a tangential plane of a surface of a semi-sphere, each fluxmeter including a superconducting quantum interference device (SQUID), said plurality of fluxmeters detecting a magnetic field component ($B_r(\theta, \phi, t)$) in an r axis direction of a biomagnetic field generated from a source within a living body, wherein a radius of said semi-sphere is set on the assumption that a shape of said source is a sphere having a center which coincides with the center of said semi-sphere and coincides with an origin of the polar coordinate system (r, $\theta$, $\phi$), the r axis direction is perpendicular to the surface of said semi-sphere, and tangential components ($B_\theta(\theta, \phi, t)$, $B_\phi(\theta, \phi, t)$) parallel to the surface of said semi-sphere of said biomagnetic field are estimated from said magnetic field component ($B_r(\theta, \phi, t)$) in the r axis direction;

operation processing means for determining a value proportional to a root of $$S(\theta, \phi, t) = \{(\delta B_r(\theta, \phi, t)/\delta\theta)^2 + (\delta B_r(\theta, \phi, t)/\delta\phi)^2\}$$

from said magnetic field component ($B_r(\theta, \phi, t)$) in the r axis direction, and for determining an isomagnetic field map obtained by connecting points at which said values proportional to said root are equal to each other; and display means for displaying said isomagnetic field map.

6. A biomagnetic field measuring apparatus comprising:

a plurality of fluxmeters disposed in parallel to a tangential plane of a surface of a semi-sphere, each fluxmeter including a superconducting quantum interference device (SQUID), said plurality of fluxmeters detecting a magnetic field component ($B_r(\theta, \phi, t)$) in an r axis direction of a biomagnetic field generated from a source within a living body, wherein a radius of said semi-sphere is set on the assumption that a shape of said source is a sphere having a center which coincides with the center of said semi-sphere and coincides with an origin of the polar coordinate system (r, $\theta$, $\phi$), the r axis direction is perpendicular to the surface of said semi-sphere, and tangential components ($B_\theta(\theta, \phi, t)$, $B_\phi(\theta, \phi, t)$) parallel to the surface of said semi-sphere of said biomagnetic field are estimated from said magnetic field component ($B_r(\theta, \phi, t)$) in the r axis direction;

operation processing means for performing computation for determining a magnetic wave form expressing a temporal change of a value proportional to a root of $$S(\theta, \phi, t) = \{(\delta B_r(\theta, \phi, t)/\delta\theta)^2 + (\delta B_r(\theta, \phi, t)/\delta\phi)^2\}$$

from said magnetic field component ($B_r(\theta, \phi, t)$) in the r axis direction, computation for integrating said magnetic wave form within a predetermined time interval to determine an integral value, and computation for determining an isointegral map obtained by connecting points at which said integral values are equal to each other; and display means for displaying said isointegral map.

7. A biomagnetic field measuring apparatus comprising:

a plurality of fluxmeters disposed in parallel to a tangential plane of a surface of a semi-sphere, each fluxmeter including a superconducting quantum interference device (SQUID), said plurality of fluxmeters detecting a magnetic field component ($B_r (\theta, \phi, t)$) in an r axis direction of a biomagnetic field generated from a source within a living body, wherein a radius of said semi-sphere is set on the assumption that a shape of said source is a sphere having a center which coincides with the center of said semi-sphere and coincides with an origin of the polar coordinate system ($r, \theta, \phi$), the r axis direction is perpendicular to the surface of said semi-sphere, and tangential components ($B_\theta (\theta, \phi, t)$, $B_\phi (\theta, \phi, t)$) parallel to the surface of said semi-sphere of said biomagnetic field are estimated from said magnetic field component ($B_r (\theta, \phi, t)$) in the r axis direction;

operation processing means for determining a magnetic field component ($B_\theta (\theta, \phi, t)$) in a $\theta$ axis direction from said magnetic field component ($B_r (\theta, \phi, t)$) in the r axis direction on the assumption that said magnetic field component ($B_\theta (\theta, \phi, t)$) in the $\theta$ axis direction is proportional to $$\delta B_r (\theta, \phi, t)/\delta\theta,$$

and for determining a magnetic field component ($B_\phi (\theta, \phi, t)$) in a $\phi$ axis direction from said magnetic field component ($B_r (\theta, \phi, t)$) in the r axis direction on the assumption that said magnetic field component ($B_\phi (\theta, \phi, t)$) in the $\phi$ axis direction is proportional to $$\delta B_r (\theta, \phi, t)/\delta\phi.$$

* * * * *